(12) United States Patent
Wei et al.

(10) Patent No.: US 11,826,431 B2
(45) Date of Patent: *Nov. 28, 2023

(54) POLYPEPTIDE-BASED OCULAR ABSORPTION ENHANCER AND APPLICATION THEREOF

(71) Applicant: Fudan University, Shanghai (CN)

(72) Inventors: Gang Wei, Shanghai (CN); Kuan Jiang, Shanghai (CN); Weiyue Lu, Shanghai (CN); Chang Liu, Shanghai (CN); Lingyu Tai, Shanghai (CN); Xin Gao, Shanghai (CN)

(73) Assignee: FUDAN UNIVERSITY, Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/410,174

(22) Filed: Aug. 24, 2021

(65) Prior Publication Data

US 2022/0008546 A1     Jan. 13, 2022

Related U.S. Application Data

(63) Continuation of application No. 16/618,915, filed as application No. PCT/CN2018/095539 on Jul. 13, 2018, now Pat. No. 11,213,591.

(30) Foreign Application Priority Data

Jun. 5, 2017  (CN) .......................... 201710414334.7

(51) Int. Cl.
| | | |
|---|---|---|
| *A61K 47/64* | (2017.01) | |
| *C07K 7/08* | (2006.01) | |
| *A61K 47/54* | (2017.01) | |
| *A61K 9/00* | (2006.01) | |

(52) U.S. Cl.
CPC ............ *A61K 47/64* (2017.08); *A61K 9/0048* (2013.01); *A61K 47/545* (2017.08); *A61K 47/549* (2017.08); *C07K 7/08* (2013.01)

(58) Field of Classification Search
CPC .................................. A61K 47/64; C07K 7/08
See application file for complete search history.

(56) References Cited

U.S. PATENT DOCUMENTS

| | | | |
|---|---|---|---|
| 11,213,591 B2 * | 1/2022 | Wei ............................. A61P 9/10 | |
| 2016/0177298 A1 * | 6/2016 | Green ................. A61K 31/5575 | 514/21.7 |

FOREIGN PATENT DOCUMENTS

| | | |
|---|---|---|
| CN | 101355970 A | 1/2009 |
| CN | 102405053 A | 4/2012 |
| WO | WO 2010091294 A2 | 8/2010 |

OTHER PUBLICATIONS

Esbjorner, E.K. et al. "Counterion-mediated Membrane Penetration: Cationic cell-penetrating Peptides Overcome Born Energy Barrier by Ion-pairing with Phospholipids," Biochimica et Biophysica Acta, vol. vol. 1768, Mar. 19, 2007 (Mar. 19, 2007), pp. 1550-1558.
Chem Res., vol. 46, Issue 12 p. 2977-2987.
For Safe Penetration from Cornea to Retina, Acta Biomaterialia, vol. 63, Sep. 18, 2017 (Sep. 18, 2017), pp. 123-134.
Liu, C. et al "Facile Noninvasive Retinal Gene Delivery Enabled by Penetratin," ACS Appl. Mater. Interfaces, vol. vol. 8, Jul. 11, 2016 (Jul. 11, 2016), pp. 19256-19267.
Liu, C. et al. "Penetratin, a Potentially Absorption Enhancer for Noninvasive Intraocular Drug Delivery", Mol. Pharmaceutics, vol. vol. 11, Feb. 12, 2014 (Feb. 12, 2014), pp. 1218-1227.
Prochiantz, A. "Getting Hydrophilic Compounds into Cells: Lessons from Homeopeptides", Cuurent Opinion in Neurobiology, vol. vol. 6, Dec. 31, 1996 (Dec. 31, 1996), pp. 629-634.
Sgolastra, F. et al. "Designing Mimics of Membrane Active Proteins", Acc. Chem. Res., vol. 46, No. (12), Dec. 17, 2013 (Dec. 17, 2013), pp. 2977-2987.
Tai, L. et al. Noninvasive Delivery of Oligonucleotide by Penetratin-modified Polyplexes to Inhibit Protein Expression of Intraocular Tumor, Nanomedicine: Nanotechnology, Biology, and Medicine, vol. 13, No. (6), Apr. 20, 2017 (Apr. 20, 2017), pp. 2091-2100.
Zhang, W. et al. "Mechanism of Penetration of Antp (43-58) into Membrane Bilayers," Biochemistry, vol. 44, No. (30), Jul. 2, 2005 (Jul. 2, 2005), pp. 10110-10118.
International Search Report from PCT/CN2018/095539 dated Sep. 17, 2018.
Office Action in Chinese Application No. 2017104143347 dated Mar. 15, 2021.
English language summary of Office Action in Chinese Application No. 2017104143347 dated Mar. 15, 2021.
Federica Sgolastra et al, Designing Mimics of Membrane Active Proteins, Acc Chem Res., vol. 46, Issue 12, p. 2977-2987—published on the web Aug. 5, 2013.
Li Li et al., Development of novel cell-penetrating peptide [Cys-CPT2,9] penetratin with high translocation ability and antitumor activity, Acta Pharmaceutica Sinica, vol. 42, Issue 5, pp. 802-808 Published Jan. 8, 2017.

(Continued)

*Primary Examiner* — Amber D Steele
(74) *Attorney, Agent, or Firm* — Lippes Mathias LLP

(57) ABSTRACT

The present disclosure belongs to the field of pharmaceutical preparations and relates to the design of a series of lipophilic derivatives by using wild-type penetrating peptide penetratin. These penetratin derivatives have a strong ability to penetrate the ocular tissues and do not cause ocular tissue toxicity. As ocular absorption enhancers, non-invasive routes could be used to achieve intraocular drug delivery and increase the ocular bioavailability of drugs. These penetratin derivatives and the ophthalmic drug delivery system constructed by them are used for eye drop administration, which could replace the intraocular injection with poor patients compliance, which greatly enhances the convenience and safety of the treatment of intraocular and fundus diseases.

18 Claims, 9 Drawing Sheets

Specification includes a Sequence Listing.

(56) References Cited

OTHER PUBLICATIONS

Liu Chang, Penetrating peptide-mediated intraocular gene delivery system, China Excellent Master's Thesis Full-text Database, Medical Science and Technology Series, No. 3, E079-134, published prior to Jun. 5, 2017.

* cited by examiner

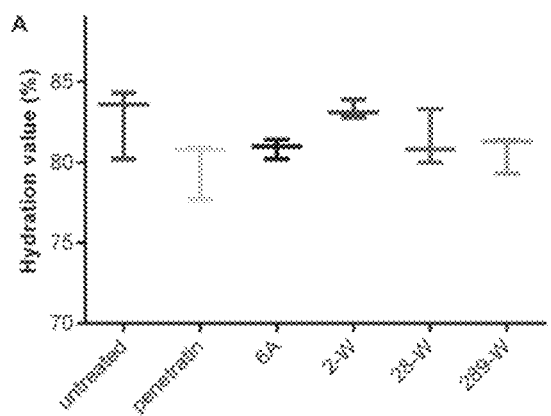
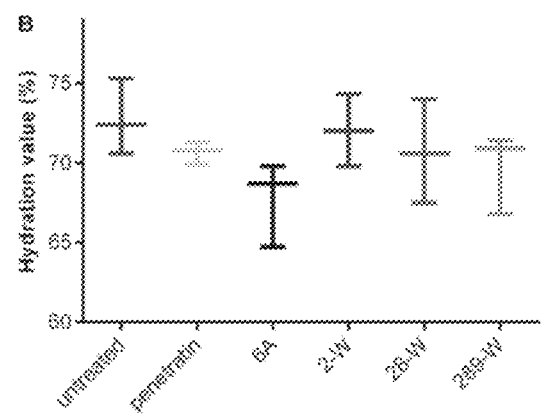
FIG. 5A　　　　　　　　　　FIG. 5B
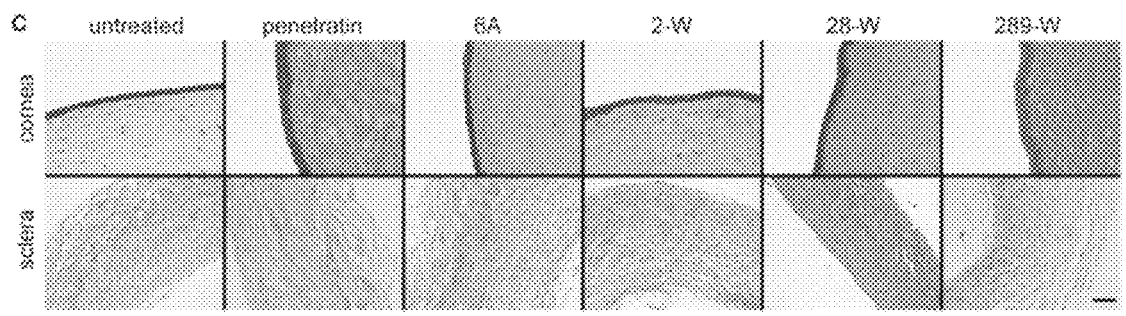
FIG. 5C

POLYPEPTIDE-BASED OCULAR ABSORPTION ENHANCER AND APPLICATION THEREOF

CROSS-REFERENCE TO RELATED APPLICATIONS

This application is a continuation of U.S. patent application Ser. No. 16/618,915, filed on Dec. 3, 2019 and having a 371(c) filing date of Jan. 22, 2020, now U.S. Pat. No. 11,213,591, which is a 371 of PCT Application No. PCT/CN2018/095539, filed Jul. 13, 2018, which claims priority to Chinese Application No. 201710414334.7, filed Jun. 5, 2017, which is incorporated by reference in its entirety.

FIELD OF THE INVENTION

The present invention belongs to the field of pharmaceutical preparations, and relates to the design of a series of lipophilic derivatives by wild-type penetrating peptide penetratin. These penetratin derivatives have very strong ability to penetrate the ocular tissues, and do not cause ocular tissue toxicity. It can be used as an ocular absorption enhancer to achieve intraocular drug delivery through a non-invasive route and to increase the ocular bioavailability of the drug. These penetratin derivatives and the ophthalmic drug delivery system thereof are used for eye drop administration, which could replace intraocular injection having poor patients compliance, which greatly enhanced the convenience and safety of the treatment of intraocular and fundus diseases.

BACKGROUND OF THE INVENTION

A sequence listing is being submitted herein as an ASCII text file with the name "UP-196345-05US_ST25.txt", created on Dec. 3, 2020, with a file size of 146,582 bytes. The material in this text file is hereby fully incorporated by reference herein.

Eye is the most important sensory organ in human body. The unique physiological structure of eye protects it from foreign substances, but it is also disadvantageous to the intraocular delivery of drugs. The physiological barriers of eye include static barriers (such as the corneal epithelium barrier, blood-ocular barrier, etc.) and dynamic barriers (such as tear washout, etc.), which are the main reasons hindering drug absorption (Drug Discovery Today, 2008, 13 (3-4): 135-143; Adv. Drug Delivery Rev., 2006, 58(11): 1131-1135). Ophthalmic preparations currently on the market are mainly in the form of eye drops, ophthalmic gels, and eye ointments. In clinical practice, after eye drops are dropped into the conjunctival sac, the drug is mainly transported into the eye through the cornea or conjunctiva. Due to the limited volume of the human conjunctival sac, coupled with tear dilution and nasolacrimal duct loss, the bioavailability of eye drops is usually less than 5%. Moreover, due to the long diffusion distance from the surface of the eye to the fundus and the convection of the aqueous humor in the eye, very little drugs (<0.001%) could reach the posterior segment of the eye (J. Controlled Release, 2014, 193: 100-112).

Systemic administration is another way of clinically treating ocular diseases, but practice has shown that due to the obstruction of the blood-ocular barrier (such as the blood-retinal barrier), it is difficult for drugs to reach the retinal tissue and vitreous cavity after systemic administration. In addition, due to the large amount of drugs entering the systemic circulation, large doses and frequent administrations also have the risk of causing systemic side effects (Invest. Ophthalmol. Visual Sci., 2000, 41 (5): 961-964).

Intraocular injection (such as intravitreal injection) and periocular injection (such as subscleral injection) are currently the most effective routes of administration for treating intraocular and fundus diseases. With these traumatic methods of administration, drugs could reach the eyes directly, with fast onset and high bioavailability, but repeated injections could cause a variety of complications (such as retinal detachment, endophthalmitis, etc.), patients are difficult to accept and have poor compliance (EYE, 2013, 27 (7): 787-794).

Comprehensive consideration of various intraocular and fundus drug delivery methods, eye drops are non-traumatic to the eye, and have low preparation cost, convenient use, and good patient compliance. Thus eye drops are clinically the most ideal ophthalmic dosage forms. However, the main problem is that the drug is difficult to be absorbed into the eye, and it is more difficult to reach fundus. The use of pharmacological methods and the introduction of absorption enhancers into the formulation of eye drops could effectively improve the efficiency of intraocular drug delivery.

Because eye is extremely sensitive, studies have reported that small molecule absorption enhancers (such as ethanol, dimethyl sulfoxide, etc.) are highly irritating to the eye and are not easily metabolized, making them unsuitable for ocular applications (Toxicol. Lett., 2001, 122 (1): 1-8). Therefore, the development of new ocular absorption enhancers is necessary.

Cell-penetrating peptides (CPPs) are short peptides that are positively charged under physiological conditions, which could mediate covalently or non-covalently linked molecules or drug delivery systems (such as double-stranded DNA, liposomes, etc.) into cells (J. Controlled Release, 2011, 155 (1SI): 26-33; Biomaterials, 2013, 34 (32): 7980-7993). The CCP penetratin derived from antennae of *Drosophila* has a strong ability to penetrate ocular tissues, and does not cause ocular cytotoxicity (Mol. Pharm. 2014, 11 (4): 1218-1227). It has been reported that penetratin acts as an absorption enhancer in several non-traumatic ocular drug delivery systems, which can mediate the reporter gene to the posterior segment of the eye and highly express in the retina (ACS Appl. Mater. Interfaces, 2016, 8 (30): 19256-19267; Nanomedicine: NBM 2017, DOI: http://dx.doi.org/10.1016/j.nano.2017.04.011; Chinese patent application for invention: CN201610560173.8). But membrane penetration ability of the wild-type penetratin still needs to be improved.

Based on published literature, a natural occurring polypeptide penetratin with strong penetrating ability to ocular tissues has been reported. This application is intended to provide a class of artificially designed and engineered penetratin derivatives. Such polypeptides are used as ocular absorption enhancers. After dripping into the conjunctival sac, they could more effectively deliver covalently or non-covalently linked drug molecules to the posterior segment of the eye, and retain good ophthalmic safety of wild-type penetratin. In addition, this method of local administration could also avoid the distribution of drugs in non-target tissues and the side effects.

SUMMARY OF THE INVENTION

The purpose of the present invention is to overcome the shortcomings of the existing absorption enhancer for ocular application, and to provide a class of artificially modified CPPs and a design method thereof. The artificial CPPs are used as an ocular absorption enhancer, which could be administered by eye drop through a non-traumatic route to deliver covalently or non-covalently linked drugs into the eye.

Ordinary eye drops have a short residence time in the conjunctival sac and have a poor absorption effect. In particular, biological macromolecular drugs such as genes, peptides, and proteins are administered through local eye drops, and the bioavailability of the eye is extremely low, and almost could not reach the posterior segment of the eyes. Intraocular injections and intraocular implants have high bioavailability, but patients have poor compliance and are likely to cause serious complications. The present invention addresses the above-mentioned problems. Based on the natural occurring CCP penetratin, a series of polypeptide derivatives with good penetrability to ocular tissues and high biosafety were designed and prepared using amino acid mutation methods. Molecules covalently linked to it, or even non-covalently linked molecules, could be delivered into the eye by a non-traumatic route. Such artificially synthesized polypeptide, as ocular absorption enhancers, could mediate drugs through the ocular absorption barrier efficiently, promote the drugs to enter the eyes and reach the posterior segment of the eyes, and thereby increase the ocular bioavailability of the drugs.

This invention provides a class of structurally modified penetratin derivatives. The amino acid sequence of the wild-type polypeptide penetratin is as follows:

RQIKIWFQNRRMKWKK          (SEQ ID NO. 1)

The applicant has unexpectedly discovered by summing up a large amount of experimental data that the penetrating ability of wild-type penetratin to the ocular tissue is improved as the hydrophobicity of the molecule increases. Therefore, the design principle of the penetratin derivatives according to the present invention is based on the premise that the basic amino acid sequence of the wild-type penetratin remains unchanged, and amino acid mutation technology is used to introduce hydrophobic amino acids into the molecule, thereby enhancing the ocular tissue penetrating ability of the obtained penetratin derivatives.

Specifically, the present invention is based on the wild-type penetratin and maintains the sequence of its original basic amino acids arginine (R), lysine (K), and original hydrophobic amino acids isoleucine (I), phenylalanine (F), tryptophan (W) and methionine (M) unchanged, and using polypeptide solid-phase synthesis technology to replace hydrophilic amino acids glutamine (Q) and asparagine (N) in penetratin molecules with hydrophobic amino acids, thereby obtained a series of polypeptide derivatives.

The penetratin derivative is characterized by having the following amino acid sequence:

RX$_1$IKIWFX$_2$X$_3$RRMKWKK          (SEQ ID NO. 2)

X$_1$, X$_2$, and X$_3$ represent hydrophobic amino acids, which are amino acids selected from natural occurring amino acids: alanine (A), valine (V), leucine (L), isoleucine (I), proline (proline, P), phenylalanine (F), tryptophan (W), methionine (M); and non-naturally occurring amino acids: α-aminobutyric acid, α-aminopentanoic acid, α-aminohexanoic acid, α-aminoheptanoic acid, etc.; and their compositions. Different hydrophilic amino acids (glutamine and asparagine) sites of the wild-type penetratin in the compositions are substituted with different hydrophobic amino acids as described above.

The amino acid sequences of the polypeptide derivatives obtained by structural modification on the basis of wild-type penetratin are shown in Table 1, where the mutated amino acid is underlined. Examples of unnatural amino acid mutations are not given in the table, and combined mutations of different hydrophobic amino acids only provided representative examples.

TABLE 1

Penetratin derivatives obtained from wild-type penetratin after structural modification

| Abbreviation | Amino acid sequence | Abbreviation | Amino acid sequence |
| --- | --- | --- | --- |
| 2-A | RAIKIWFQNRRMKWKK (SEQ ID NO. 3) | 2-V | RVIKIWFQNRRMKWKK (SEQ ID NO. 4) |
| 8-A | RQIKIWFANRRMKWKK (SEQ ID NO. 5) | 8-V | RQIKIWFVNRRMKWKK (SEQ ID NO. 6) |
| 9-A | RQIKIWFQARRMKWKK (SEQ ID NO. 7) | 9-V | RQIKIWFQVRRMKWKK (SEQ ID NO. 8) |
| 28-A | RAIKIWFANRRMKWKK (SEQ ID NO. 9) | 28-V | RVIKIWFVNRRMKWKK (SEQ ID NO. 10) |
| 29-A | RAIKIWFQARRMKWKK (SEQ ID NO. 11) | 29-V | RVIKIWFQVRRMKWKK (SEQ ID NO. 12) |
| 89-A | RQIKIWFAARRMKWKK (SEQ ID NO. 13) | 89-V | RQIKIWFVVRRMKWKK (SEQ ID NO. 14) |
| 289-A | RAIKIWFAARRMKWKK (SEQ ID NO. 15) | 289-V | RVIKIWFVVRRMKWKK (SEQ ID NO. 16) |
| 2-L | RLIKIWFQNRRMKWKK (SEQ ID NO. 17) | 2-I | RIIKIWFQNRRMKWKK (SEQ ID NO. 18) |
| 8-L | RQIKIWFLNRRMKWKK (SEQ ID NO. 19) | 8-I | RQIKIWFINRRMKWKK (SEQ ID NO. 20) |
| 9-L | RQIKIWFQLRRMKWKK (SEQ ID NO. 21) | 9-I | RQIKIWFQIRRMKWKK (SEQ ID NO. 22) |
| 28-L | RLIKIWFLNRRMKWKK (SEQ ID NO. 23) | 28-I | RIIKIWFINRRMKWKK (SEQ ID NO. 24) |
| 29-L | RLIKIWFQLRRMKWKK (SEQ ID NO. 25) | 29-I | RIIKIWFQIRRMKWKK (SEQ ID NO. 26) |
| 89-L | RQIKIWFLLRRMKWKK (SEQ ID NO. 27) | 89-I | RQIKIWFIIRRMKWKK (SEQ ID NO. 28) |
| 289-L | RLIKIWFLLRRMKWKK (SEQ ID NO. 29) | 289-I | RIIKIWFIIRRMKWKK (SEQ ID NO. 30) |
| 2-P | RPIKIWFQNRRMKWKK (SEQ ID NO. 31) | 2-F | RFIKIWFQNRRMKWKK (SEQ ID NO. 32) |
| 8-P | RQIKIWFPNRRMKWKK (SEQ ID NO. 33) | 8-F | RQIKIWFFNRRMKWKK (SEQ ID NO. 34) |
| 9-P | RQIKIWFQPRRMKWKK (SEQ ID NO. 35) | 9-F | RQIKIWFQFRRMKWKK (SEQ ID NO. 36) |
| 28-P | RPIKIWFPNRRMKWKK (SEQ ID NO. 37) | 28-F | RFIKIWFFNRRMKWKK (SEQ ID NO. 38) |
| 29-P | RPIKIWFQPRRMKWKK (SEQ ID NO. 39) | 29-F | RFIKIWFQFRRMKWKK (SEQ ID NO. 40) |
| 89-P | RQIKIWFPPRRMKWKK (SEQ ID NO. 41) | 89-F | RQIKIWFFFRRMKWKK (SEQ ID NO. 42) |

TABLE 1-continued

Penetratin derivatives obtained from wild-type penetratin after structural modification

| Abbreviation | Amino acid sequence | Abbreviation | Amino acid sequence |
|---|---|---|---|
| 289-P | RPIKIWFPPRRMKWKK (SEQ ID NO. 43) | 289-F | RFIKIWFFFRRMKWKK (SEQ ID NO. 44) |
| 2-W | RWIKIWFQNRRMKWKK (SEQ ID NO. 45) | 2-M | RMIKIWFQNRRMKWKK (SEQ ID NO. 46) |
| 8-W | RQIKIWFWNRRMKWKK (SEQ ID NO. 47) | 8-M | RQIKIWFMNRRMKWKK (SEQ ID NO. 48) |
| 9-W | RQIKIWFQWRRMKWKK (SEQ ID NO. 49) | 9-M | RQIKIWFQMRRMKWKK (SEQ ID NO. 50) |
| 28-W | RWIKIWFWNRRMKWKK (SEQ ID NO. 51) | 28-M | RMIKIWFMNRRMKWKK (SEQ ID NO. 52) |
| 29-W | RWIKIWFQWRRMKWKK (SEQ ID NO. 53) | 29-M | RMIKIWFQMRRMKWKK (SEQ ID NO. 54) |
| 89-W | RQIKIWFWWRRMKWKK (SEQ ID NO. 55) | 89-M | RQIKIWFMMRRMKWKK (SEQ ID NO. 56) |
| 289-W | RWIKIWFWWRRMKWKK (SEQ ID NO. 57) | 289-M | RMIKIWFMMRRMKWKK (SEQ ID NO. 58) |
| 2-A, 8-V | RAIKIWFVNRRMKWKK (SEQ ID NO. 59) | 2-F, 9-W | RFIKIWFQWRRMKWKK (SEQ ID NO. 60) |
| 2-V, 8-A | RVIKIWFANRRMKWKK (SEQ ID NO. 61) | 2-W, 9-F | RWIKIWFQFRRMKWKK (SEQ ID NO. 62) |
| 2-V, 9-L | RVIKIWFQLRRMKWKK (SEQ ID NO. 63) | 2-W, 9-M | RWIKIWFQMRRMKWKK (SEQ ID NO. 64) |
| 2-L, 9-V | RLIKIWFQVRRMKWKK (SEQ ID NO. 65) | 2-M, 9-W | RMIKIWFQWRRMKWKK (SEQ ID NO. 66) |
| 2-L, 9-I | RLIKIWFQIRRMKWKK (SEQ ID NO. 67) | 2-M, 8-W, 9-Y | RMIKIWFWYRRMKWKK (SEQ ID NO. 68) |
| 2-I, 9-L | RIIKIWFQLRRMKWKK (SEQ ID NO. 69) | 2-W, 8-Y, 9-P | RWIKIWFYPRRMKWKK (SEQ ID NO. 70) |
| 2-I, 8-P | RIIKIWFPNRRMKWKK (SEQ ID NO. 71) | 2-Y, 8-P, 9-I | RYIKIWFPIRRMKWKK (SEQ ID NO. 72) |
| 2-P, 8-I | RPIKIWFINRRMKWKK (SEQ ID NO. 73) | 2-P, 8-I, 9-L | RPIKIWFILRRMKWKK (SEQ ID NO. 74) |
| 2-P, 8-F | RPIKIWFFNRRMKWKK (SEQ ID NO. 75) | 2-I, 8-L, 9-V | RIIKIWFLVRRMKWKK (SEQ ID NO. 76) |
| 2-F, 8-P | RFIKIWFPNRRMKWKK (SEQ ID NO. 77) | 2-L, 8-V, 9-A | RLIKIWFVARRMKWKK (SEQ ID NO. 78) |

The penetratin derivatives described in the present invention could be linked with a drug having a diagnostic or therapeutic effect through an amide bond, a disulfide bond, a tetrahydrothiazole ring or other chemical bonds. One or more amino acids could also be used as a bridge, or other bifunctional groups could be used as a bridge to connect with a drug having a diagnostic or therapeutic effect.

The above-mentioned drugs for diagnosis or treatment are selected from, but not limited to, one of the following drugs or a combination thereof:

1) Drugs for treating cataract: selected from vitamin C, vitamin E, piroxixin, glutathione, bendazac lysine, etc.;

2) Drugs for treating bacterial endophthalmitis: selected from vancomycin, ceftazidime, isepamicin, neomycin, gentamicin, erythromycin, dexamethasone, trovafloxacin, cefuroxime sodium, minocycline, etc.;

3) Drugs for treating fungal endophthalmitis: selected from voriconazole, nystatin, amphotericin B, etc.;

4) Drugs for treating glaucoma: selected from pilocarpine, carbachol, dipivefrin, timolol, betaxolol, metipranolol, levobunolol, carteolol, dorzolamide, brizolamide, brimonidine, Latanoprost, travoprost, bimatoprost, bemeprost, tafluprost, etc.;

5) Anti-metabolic drugs: selected from fluorouracil, mitomycin, etc.;

6) Drugs for treating uvea disease: selected from glucocorticoids, acyclovir, penicillin, etc.;

7) Drugs for treating retinal diseases: selected from triamcinolone acetonide, etc.;

8) Drugs for treating optic nerve diseases: selected from prednisolone, vitamin B1, vitamin B12, niacin and the like.

The penetratin derivatives described in the present invention could also be modified on the surface of drug delivery systems such as liposomes, micelles, and nanoparticles through bifunctional bridging molecules, such as bifunctional polyethylene glycol (PEG), so that these drug delivery systems contains the above-mentioned drugs to achieve intraocular delivery of the above-mentioned drugs.

The penetratin derivatives described in the present invention retain the characteristic that the wild-type penetratin has a positive charge under physiological conditions. The penetratin derivatives could also self-assemble to form a nano-complex through electrostatic interaction with biological macromolecular drugs such as genes, polypeptides, and proteins with negative charges under physiological conditions; or self-assemble to form a nanocomplex with biological macromolecular drugs such as genes, polypeptides, and proteins with negative charges under physiological conditions in the presence of cationic polymers such as polyethyleneimine (PEI), polylysine (DGLs), polyamide-amine dendrimers (PAMAM), etc.; to realize the intraocular delivery of the above-mentioned biological macromolecular drugs.

The above-mentioned biological macromolecular drugs are selected from, but not limited to, one of the following drugs or a combination thereof:

1) Gene drugs: selected from plasmid DNA (pDNA), pegaptanib, bevasiranib, antisense oligonucleotide, etc.;

2) Monoclonal antibody drugs: selected from Bevacizumab, Ramucirumab, etc.;

3) Other polypeptide and protein drugs: selected from the anti-vascular endothelial growth factor (anti-VEGF) fusion protein Conbercept, epidermal growth factor (EGF), defensin, interferon and cyclosporin.

The penetratin derivatives described in the present invention form a covalent complex with a drug having a diagnostic or therapeutic effect, or modified on the surface of drug delivery systems such as liposomes, micelles, and nanoparticles that contain diagnostic or therapeutic drugs, or self-assemble with bio-macromolecules drugs such as genes, polypeptides and proteins with negative charges under physiological conditions to form non-covalent nanocomplexes, after intraocular administration through the conjunctival sac, it could promote the drug to pass through many ocular absorption barriers (cornea, conjunctiva, sclera, etc.) into the eye, even the chemical drugs or biomacromolecules drugs such as genes, polypeptides, and protein they carry are delivered to the retina in the posterior segment of the eye. In the covalent complex, surface-modified nano drug delivery system, or non-covalent nanocomplex constructed using the penetratin derivative, the concentration of the penetratin derivative is 1 nM-500 μM, preferably 10 nM-300 μM, and more preferably 100 nM-100 μM. This intraocular drug delivery system administered through a non-traumatic route helps to promote drug absorption in the eye, improve the eye bioavailability of chemical drugs and biomacromolecules, and could be used clinically as an alternative to intraocular injection and other administration with low compliance.

In order to show the ocular absorption promotion effect of the penetratin derivatives described in the present invention on a chemical drug covalently connected thereto, taking a tryptophan (W)-monosubstituted penetratin derivative as an example, one additional lysine (K) was attached to the C-terminus of the tryptophan-substituted penetratin derivative and a fluorescent probe carboxyfluorescein (FAM) was linked to the amino side chain of lysine to form a covalent complex. Through a series of in vitro and in vivo experiments, the present invention investigated the ocular cell uptake ability of penetratin derivative-modified fluorescent probes, permeability of ocular tissues in vitro and absorption and distribution in the eye of living animals after intraocular administration through intraconjunctival sac. The results show that compared with the wild-type penetratin, the tryptophan-substituted penetratin derivative has significantly enhanced ocular absorption promotion ability.

More importantly, the applicant found that the penetrating ability of penetratin derivatives to ocular tissue is related to its hydrophobicity (lipophilicity). The stronger the hydrophobicity (lipophilicity), the stronger penetrating ability of penetratin derivatives to ocular tissue. Therefore, penetratin derivatives prepared using other hydrophobic amino acids would also achieve enhanced ocular absorption promotion effects. Moreover, the applicant confirmed that penetratin derivatives could effectively deliver fluorescent probes into the eye, and if fluorescent probes were replaced with other diagnostic or therapeutic drugs, the same intraocular delivery effect would be achieved.

In order to show the eye absorption promotion effect of penetratin derivative in the present invention on nano-drug carrier and bio-macromolecule drug through non-covalent binding thereto, taking a phenylalanine (F)-monosubstituted penetratin derivative as an example, and using antisense oligonucleotides as biological macromolecular drug models, a non-covalent complex containing antisense oligonucleotide was constructed in the presence of polyamide-amine dendrimer (PAMAM) and hyaluronic acid (HA). Through a series of in vitro and in vivo experiments, the present invention investigated the ocular cell uptake ability of penetratin derivative-modified non-covalent complexes, permeability of ocular tissues in vitro and absorption and distribution in the eye of living animals after intraocular administration through intraconjunctival sac. The results show that compared with the wild-type penetratin, the phenylalanine substituted penetratin derivative has significantly enhanced ocular absorption promotion ability.

The advantages of the penetratin derivatives in the present invention are that compared to small molecule absorption enhancers that are rarely used in the eye due to safety issues, such polypeptide absorption enhancers are easy to degrade and thus have better biological safety. On the other hand, polypeptide absorption enhancers are easy to be modified to achieve different application goals, and the penetratin derivatives of the present invention have stronger ocular absorption promotion capabilities than wild-type penetratin of natural origin.

BRIEF DESCRIPTION OF THE DRAWINGS

FIG. 4B is a fluorescent section of DAPI staining of the isolated tissues of the blank group and the experimental group, and scale bar represents 100 μm.

FIGS. 5A-5C: Evaluation of in vitro tissue toxicity of complexes of penetratin derivatives covalently linked with small molecules
Wherein FIG. 5A is the corneal hydration value of the blank group and the penetratin derivative-FAM covalent complex group; FIG. 5B is the scleral hydration value of the blank group and the penetratin derivative-FAM covalent complex group; and FIG. 5C is HE stained sections of isolated tissues from the blank group and penetratin derivative-FAM covalent complex group, and scale bar represents 100 μm.

FIGS. 6A-6C: Distribution of complexes of penetratin derivatives covalently linked with small molecules in the eyes of living mice
Wherein FIG. 6A shows the distribution of penetratin derivative-FAM covalent complexes in the anterior (corneal) and posterior (retinal) segments of mice at different time points (10 min, 0.5 h, 1 h, 2 h, 4 h, 6 h) after administration of the conjunctival sac; FIG. 6B shows the distribution of the penetratin derivative-FAM covalent complex in the anterior segment (cornea) and posterior segment (retina) of the mouse 10 min after administration of the conjunctival sac; FIG. 6C is the result of semi-quantitative analysis of intraocular distribution of penetratin derivative-FAM covalent complex 10 min, 1 h, and 6 h after administration.

FIGS. 7A-7B: Ocular absorption of a non-covalent complex of a Penetratin derivative and an antisense oligonucleotide drug
Wherein FIG. 7A shows the distribution of each group of non-covalent complexes (ASO/PG5, ASO/PG5/HA, ASO/PG5/HA/Pene) in mice at different time points (1 h, 2 h, 6 h, and 8 h) after administration of the conjunctival sac; FIG. 7B shows the distribution of each group of green fluorescent labeled ASO in each area of the retina.

DETAILED DESCRIPTION OF THE INVENTION

Figure 1:
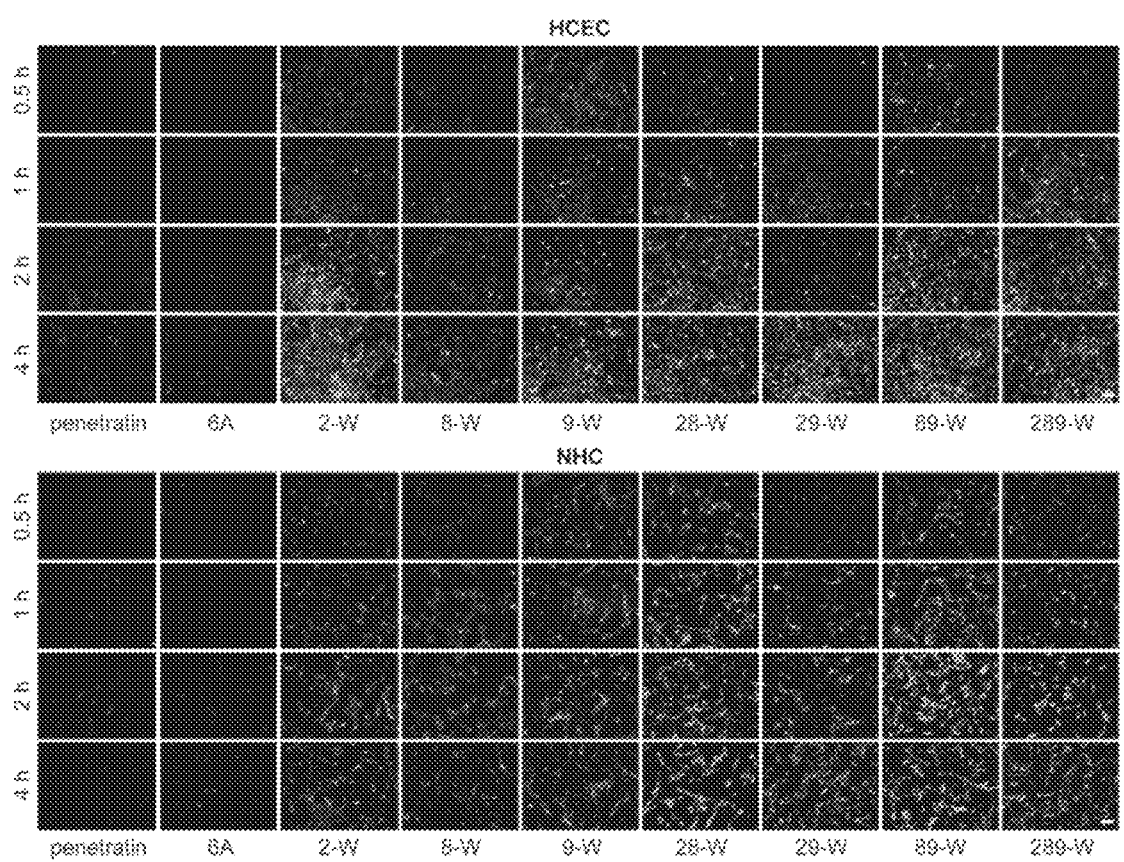
FIG. 1: Qualitative evaluation of cellular uptake of complexes of penetratin derivatives covalently linked with small molecules
Wherein human corneal epithelial cells and human conjunctival epithelial cells were incubated with penetratin derivative-FAM covalent complex (100 nM) for 0.5 h, 1 h, 2 h, and 4 h, respectively, and scale bar represents 100 μm.
Figure 2:
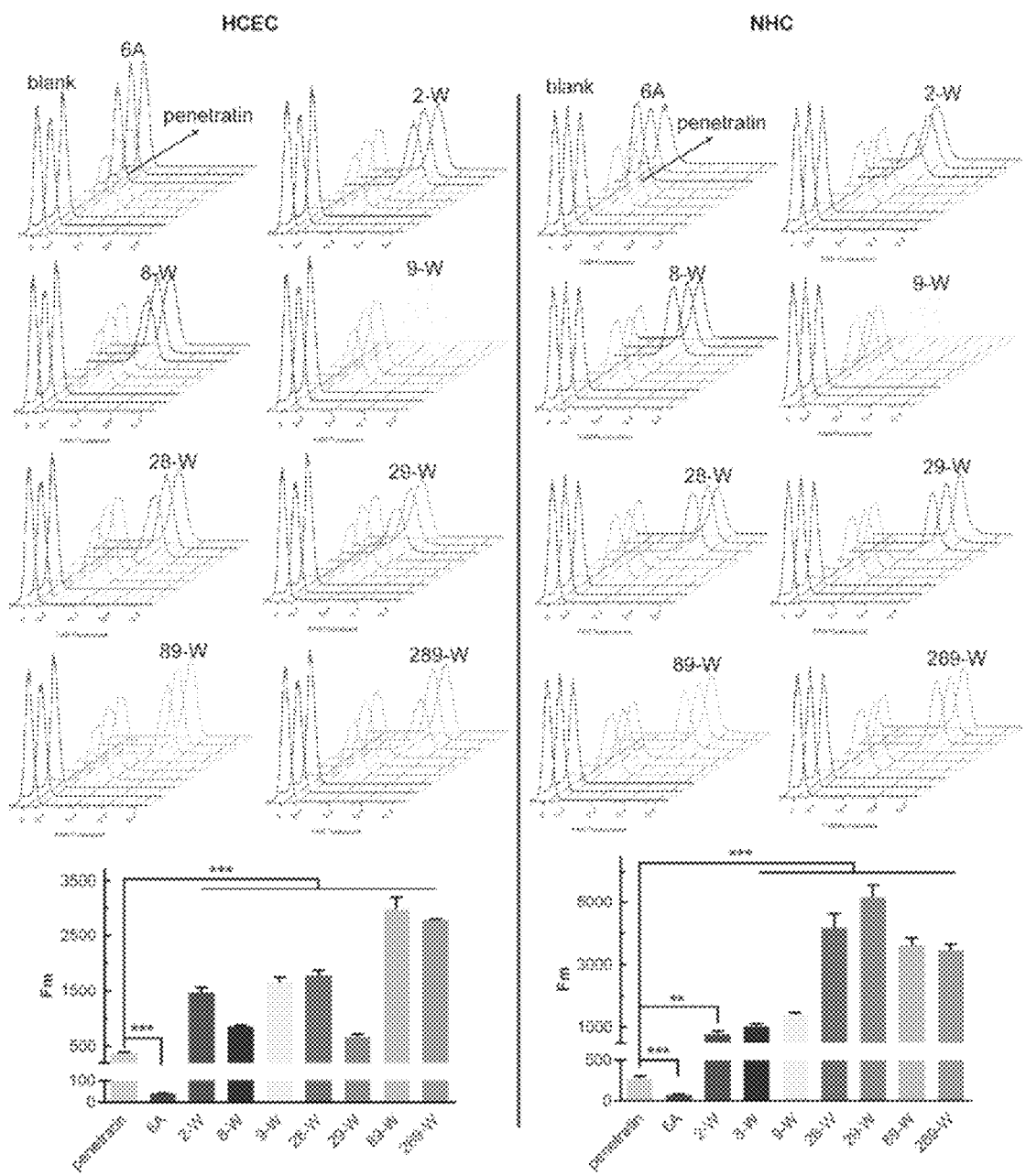
FIG. 2: Qualitative evaluation of cellular uptake of complexes of penetratin derivatives covalently linked with small molecules
Wherein human corneal epithelial cells and human conjunctival epithelial cells were incubated with penetratin derivative-FAM covalent complexes for 4 h, and Fm was the average fluorescence intensity of the cells.
Figure 3:
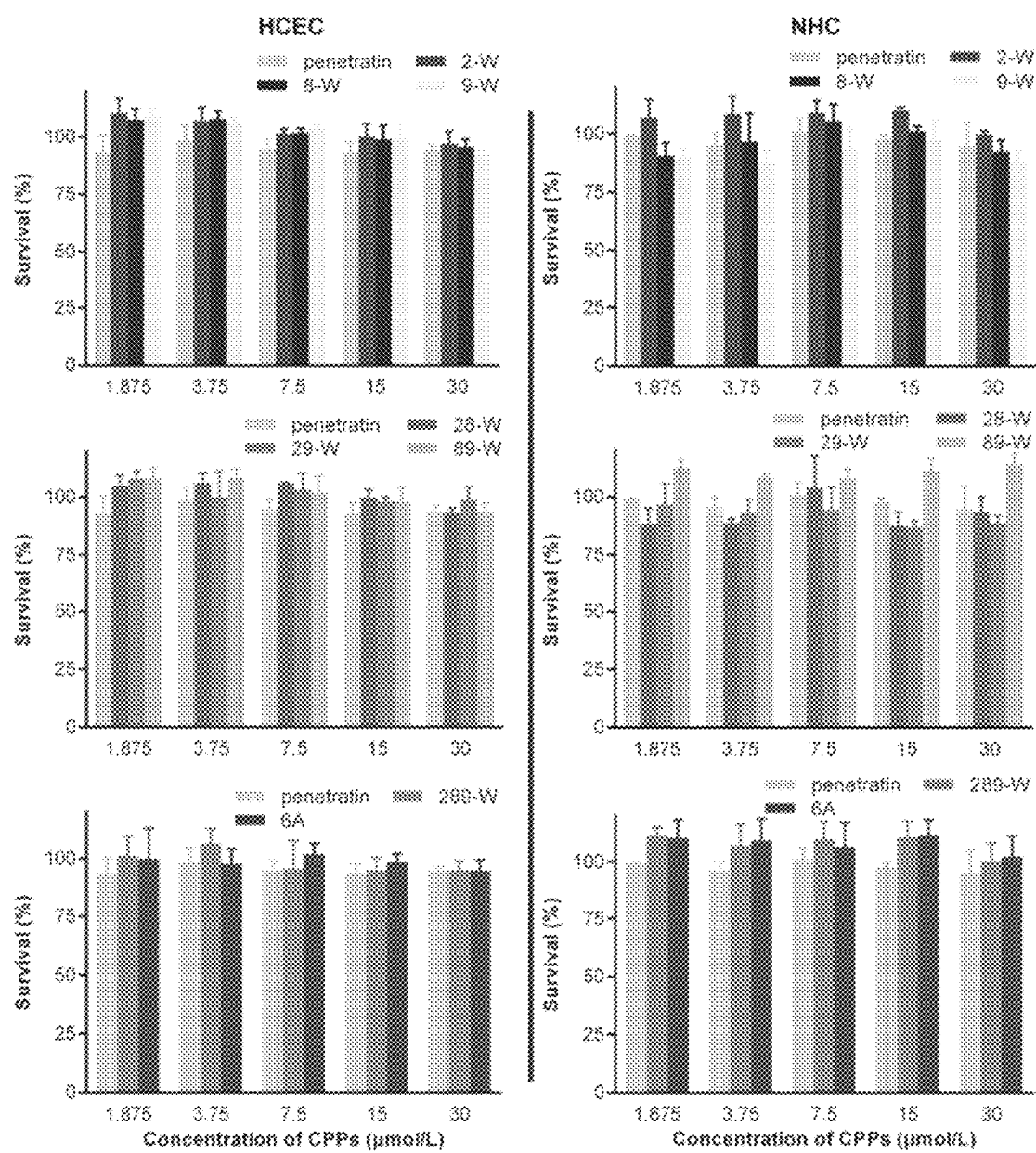
FIG. 3: Evaluation of the cytotoxicity of penetratin derivatives
Wherein human corneal epithelial cells and human conjunctival epithelial cells were incubated with penetratin derivatives for 12 h, and the cell survival rate of the experimental group relative to the negative control group was measured by MTT method.

The present invention is further illustrated below with reference to specific embodiments of the present invention, but the scope of protection is not limited.

Example 1

Preparation of covalently linked complexes of Penetratin derivatives and small molecular substances: based on the structure of wild-type penetratin, the sequences of the original basic amino acid and hydrophobic amino acid were kept unchanged, then peptide solid-phase synthesis technology was used to replace hydrophilic amino acids glutamine (Q) and asparagine (N) in penetratin molecules with hydrophobic tryptophan (W), respectively, thereby a series of polypeptide derivatives were obtained. One additional lysine (K) was attached to the C-terminus of the tryptophan-substituted penetratin derivative, and a fluorescent probe carboxyfluorescein (FAM) was linked to the amino side chain of lysine to form a covalent complex, the amino acid sequence of the covalent complex is shown in Table 2.

At the same time, the sequences of the original basic amino acid and hydrophilic amino acid the wild-type penetratin were kept unchanged, then peptide solid-phase synthesis technology was used to replace the more hydrophobic isoleucine (I), phenylalanine (F), tryptophan (W), and methionine (M) in penetratin molecules with alanine (A), so as to obtain a hydrophilic penetratin derivative 6A, it was further fluorescently labeled with FAM as a hydrophilic control polypeptide.

TABLE 2

Amino acid sequences of covalent complexes of Penetratin derivatives and fluorescent probes

| Abbreviation | Amino acid sequence |
| --- | --- |
| Penetratin | RQIKIWFQNRRMKWKKK-FAM (SEQ ID NO. 79) |
| 2-W | RWIKIWFQNRRMKWKKK-FAM (SEQ ID NO. 80) |
| 8-W | RQIKIWFWNRRMKWKKK-FAM (SEQ ID NO. 81) |
| 9-W | RQIKIWFQWRRMKWKKK-FAM (SEQ ID NO. 82) |
| 28-W | RWIKIWFWNRRMKWKKK-FAM (SEQ ID NO. 83) |
| 29-W | RWIKIWFQWRRMKWKKK-FAM (SEQ ID NO. 84) |
| 89-W | RQIKIWFWWRRMKWKKK-FAM (SEQ ID NO. 85) |

TABLE 2-continued

Amino acid sequences of covalent complexes of Penetratin derivatives and fluorescent probes

| Abbreviation | Amino acid sequence |
| --- | --- |
| 289-W | RWIKIWFWWRRMKWKKK-FAM (SEQ ID NO. 86) |
| 6A | RQAKAAAQNRRAKAKKK-FAM (SEQ ID NO. 87) |

Using the above method, the applicant also prepared penetratin derivatives substituted by natural amino acids and non-natural amino acids such as Alanine (A), Valine (V), Leucine (L), Isoleucine (I), Proline (P), Phenylalanine (F), Tryptophan (W), Methionine (M), α-aminobutyric acid, α-aminopentanoic acid, α-aminohexanoic acid, α-aminoheptanoic acid and their combination. The amino acid sequences are shown in Table 1.

Using the above methods, the applicant also connected the drugs used to treat cataracts, bacterial endophthalmitis, fungal endophthalmitis, glaucoma, antimetabolite, uveal disease, retinal disease and optic nerve disease with the penetratin derivative through a covalent bond to form a covalent complex of the penetratin derivative and the small molecule drug.

Example 2

Qualitative evaluation of cell uptake of the covalently linked complex of Penetratin derivatives and small molecular substances: well-growing human corneal epithelial cells (HCEC) and human conjunctival epithelial cells (NHC) were inoculated into 24-well plates at $5\times10^3$ cells/cm$^2$, respectively. In the well plate, the culture solution was changed once a day after inoculation, and the experiment was performed after 2 to 3 days of culture. After discarding the culture solution, washing it three times with sterile PBS, adding serum-free DMEM solution containing 100 nM complex of penetratin derivative and FAM, and incubating at 37° C. and 5% $CO_2$ for a period of time (0.5 h, 1 h, 2 h and 4 h). After the treatment, the solution was discarded, and the positively charged adsorbed substance was washed away with a PBS buffer solution containing 0.02 mg/mL heparin sodium, observed under inverted fluorescence microscope after staining cell nuclei with diimidylphenylindole (DAPI).

The results showed that for wild-type penetratin, the FAM fluorescence signal was still weak after 4 h incubation, and for the hydrophilic penetratin derivative 6A, the FAM fluorescence signal was weaker. Obviously, the lipophilic penetratin derivatives have strong FAM fluorescence signals, particularly the penetratin derivatives 9-W, 28-W, 89-W, and 289-W. After 1 h of administration, a clear FAM fluorescence signal was observed from the cells. And with the increase of incubation time, the fluorescence signal of FAM also increased. It is shown that using hydrophobic amino acids to replace the original hydrophilic amino acids in penetratin molecules is beneficial to promote the uptake of small molecules carried by polypeptides by cells, and increased hydrophilicity reduces cell uptake.

Example 3

Quantitative evaluation of cell uptake of the covalently linked complex of Penetratin derivatives and small molecular substances: well-growing HCEC and NHC cells were inoculated into 24-well plates at $5\times10^3$ cells/cm$^2$, respectively. In the well plate, the culture solution was changed once a day after inoculation, and the experiment was performed after 2 to 3 days of culture. After discarding the culture solution, washing it three times with sterile PBS, adding serum-free DMEM solution containing 3 µM complexes of penetratin derivative and FAM, and incubating at 37° C. and 5% $CO_2$ for 4 h. When finished, the solution was discarded, and the positively charged adsorbed substance was washed away with a PBS buffer solution containing 0.02 mg/mL heparin sodium, the cells were digested, resuspended in 200 µL of sterile PBS buffer solution, and flow cytometry was performed after pipetting. The cell count of each sample was 104. Unadministered cells served as a negative control group.

In HCEC cells, the cellular uptake of complex of lipophilic penetratin derivative and FAM was significantly higher than that of complex of wild-type penetratin and FAM ($p<0.001$), and the average fluorescence intensity is 1.7 (29-W)~7.7 (89-W) times of the wild-type penetratin group. The average fluorescence intensity of the hydrophilic penetratin derivative 6A was only 1/10 of that of the wild-type penetratin group ($p<0.001$). For NHC cells, the average fluorescence intensity of hydrophobic penetratin derivatives is 2.8 (2-W) to 18.9 (29-W) times that of the wild-type penetratin ($p<0.01$). The average fluorescence intensity of hydrophilic penetratin derivatives is only ¼ of that of the wild-type penetratin ($p<0.001$). Based on the above results, the cellular uptake of lipophilic penetratin derivatives was significantly higher than that of the wild-type penetratin for both HCEC and NHC cells, while the cellular uptake that of hydrophilic penetratin derivatives was significantly lower than that of the wild-type penetratin, consistent with the results of qualitative uptake.

Example 4

Evaluation of cytotoxicity of Penetratin derivatives: HCEC and NHC cells in good logarithmic growth state were plated in 60 inner wells of a 96-well plate at a concentration of 3,000 cells/well, respectively, and the edges were filled with sterile PBS buffer solution. Incubated at 37° C. and 5% $CO_2$ until the cell monolayer were spread over the bottom of the plate. The culture solution was discarded and washed it 3 times with sterile PBS buffer, and then added 200 µL of culture solution containing penetratin derivatives with different concentrations. After incubated in the cell incubator for 12 hours, the culture solution was discarded and washed 3 times with sterile PBS buffer, and complete medium was added to continue incubating for 12 hours. 20 µL of thiazole blue (MTT) solution (5 mg/mL) was then added to each well. After incubated for 4 hours, the liquid was carefully discarded. After washed 3 times with PBS buffer, 150 µL of dimethyl sulfoxide (DMSO) was added to each well. After shaking at low speed for 20 minutes on a shaker, the absorbance of each well was measured at OD490 nm on a microplate reader. The blank zeroing wells (medium, MTT, DMSO) and negative control wells (cell, medium, MTT, DMSO) were set at the same time.

The results showed that under the conditions of the concentration range to be tested (o be M), the cell growth status did not change significantly, and penetratin and its derivatives showed no toxic effect on HCEC and NHC cells.

Example 5

Evaluation of in vitro tissue permeability of the covalently linked complex of Penetratin derivatives and small molecular substances: the experimental rabbits were anesthetized with pentobarbital sodium (30 mg/kg), which is injected via ear vein, and sacrificed by injection with excessive chloral hydrate (150 mg/kg). After separation of the conjunctiva, carefully removed the entire eyeball, make a circumcision at about 2 mm from the limbus of cornea and remove the cornea, and removed the iris and other tissues to obtain an experimental cornea. The rest of the eyeballs were removed from the retina and other tissues to obtain an experimental sclera. Both the cornea and sclera were carefully washed with Ringer's solution 3 times before use. The experiment was started within 30 min after the animals were sacrificed. The freshly isolated cornea and sclera were carefully sandwiched between two diffusion cells, with the epithelial surface facing a diffusion cell (supply cell) on the left, the diffusion window diameter was 10.25 mm, and the diffusion area was 0.825 cm$^2$. 3.5 mL of Ringer's solutions were added to the supply cell and a receiving cell on the right, respectively. Circulating water was passed therein, and the water temperature was kept at 34° C.±0.5° C. After the system was equilibrated for 10 minutes, the solution in the supply cell was removed, and a solution of the complex of Penetratin derivative and FAM was added at a concentration of 7.5 µM. The entire diffusion device was placed on the diffuser, magnetic stirring was maintained, the constant temperature water bath was maintained at 34° C.±0.5° C., and a mixed gas ($O_2$:$CO_2$=95:5, volume ratio) was passed into the diffusion medium. After the experiment was started, samples were taken at preset time points, 500 µL each time in the receiving cell, and 500 µL of fresh Ringer's solution was immediately added. Immediately after the experiment, the fluorescence intensity of the sample was measured. After removing the cornea and sclera, carefully rinsed the surface 3 times with Ringer's solution to remove the parts other than the diffuse surface. After the remaining tissue was fixed with Davidson's solution, frozen sections of DAPI staining were used to observe the tissue distribution of polypeptide-linked fluorescent probe.

Figure 4A:
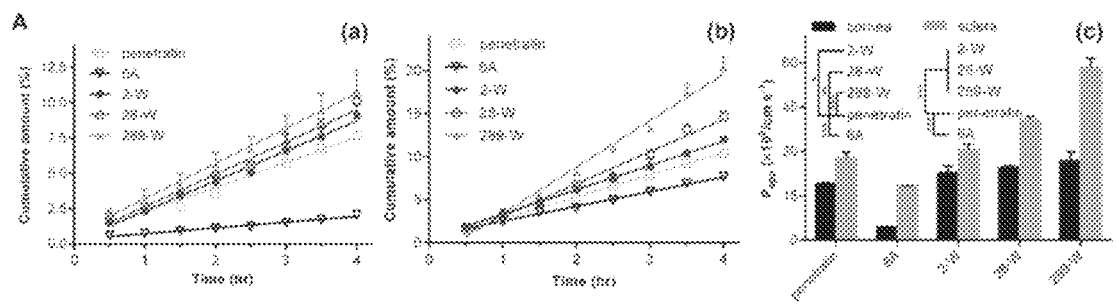
FIGS. 4A-4B: Evaluation of the penetrating ability of isolated ocular tissues of complexes of penetratin derivatives covalently linked with small molecules
Wherein in FIG. 4A, (a) is a penetration curve of penetratin derivative-FAM covalent complex on isolated cornea of rabbit eyes, (b) is a penetration curve of penetratin derivative-FAM covalent complex on isolated sclera of rabbit eyes, (c) is the apparent permeability coefficient.
Figure 4B:
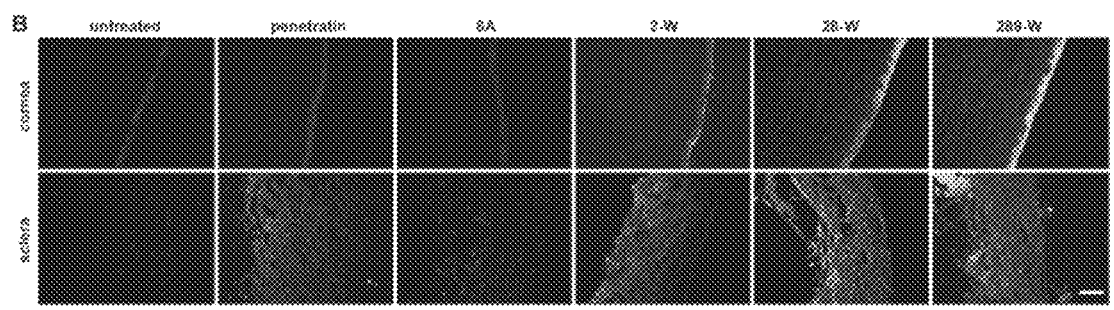

The results in FIG. 4A show that the process of the fluorescent probe connected to the polypeptide permeating the cornea and sclera in vitro is a time-dependent linear process. According to the apparent transmission coefficient ($P_{app}$) values obtained from each curve, for isolated cornea, the $P_{app}$ values of lipophilic derivatives 2-W, 28-W, and 289-W are 1.2, 1.3, and 1.4 times that of wild-type penetratin, respectively ($p<0.05$), while the hydrophilic derivative 6A is only ⅕ of the wild-type penetratin ($p<0.001$). For isolated sclera, the $P_{app}$ values of derivatives 2-W, 28-W, and 289-W were 1.1, 1.5, and 2.1 times that of wild-type penetratin ($p<0.001$), while 6A was only ⅔ of wild-type penetratin ($P<0.001$). The isolated corneal and scleral fluorescence sections after DAPI staining in FIG. 4B show that no green fluorescence is seen in the blank tissue section, indicating that the tissue has no fluorescent background interference. In the cornea in vitro, compared with the wild-type penetratin group, the lipophilic penetratin derivative-treated cornea has stronger fluorescence intensity, and the stronger the lipophilicity, the more the amount of corneal entry, while the hydrophilic penetratin derivative 6A group had no obvious fluorescence signal. In the isolated sclera, the fluorescence signal of the lipophilic derivative group was stronger than that of the wild-type penetratin group, while 6A was significantly weaker than that of the penetratin group.

Example 6

Evaluation of in vitro tissue toxicity of covalently linked complexes of Penetratin derivatives and small molecular substances: a portion of the tissue fixed with Davidson's solution is taken for paraffin section stained with hematoxylin-eosin (HE), then the integrity of the tissue after the permeability experiment is observed; another portion of the tissue is taken, the surface moisture of which is absorbed with filter paper, weighed and recorded as $m_0$, and then dried in an oven at 60° C. for 48 h, recorded as $m_t$ after weighing, the tissue hydration value is calculated according to the following formula:

$$\Delta H = (m_0 - m_t)/m_0 \times 100\%$$

The results in FIG. 5A show that the hydration values of the cornea and sclera in vitro treated with penetratin derivatives are not significantly different from those of the untreated fresh cornea and sclera, and are consistent with normal values reported in the literature. This showed that penetratin derivatives had no toxic effect on isolated ocular tissues at the concentration of 7.5 M.

The results of HE stained sections in FIG. 5B show that all cornea treated with penetratin derivatives maintained an intact corneal epithelial structure without cavitation or damage. All sclera treated with penetratin derivatives also maintained an intact structure without fiber breakage. It shows that penetratin derivative has no toxic effect on cornea and sclera in vitro at 7.5 μM concentration.

Example 7

Evaluation of intraocular distribution of the covalently linked complex of Penetratin derivatives and small molecules: 5 μL of a solution of complex of penetratin derivative and FAM (concentration 30 μM) was dripped into the conjunctival sac of male mice, and the eyelids were gently closed to distribute the solution evenly. The solution was administered every 10 minutes for a total of 3 times, and taking the time of the last administration as zero time. At a preset time point, mice were killed by intraperitoneal injection of excessive chloral hydrate, and the eyeballs of the mice were removed, fixed with Davidson's solution for 0.5 h, and embedded. Frozen longitudinal sections of eyeballs were prepared and the nuclei were stained with DAPI, and the distribution of polypeptides in the eye parts was observed under an inverted fluorescence microscope.

Figure 6A:
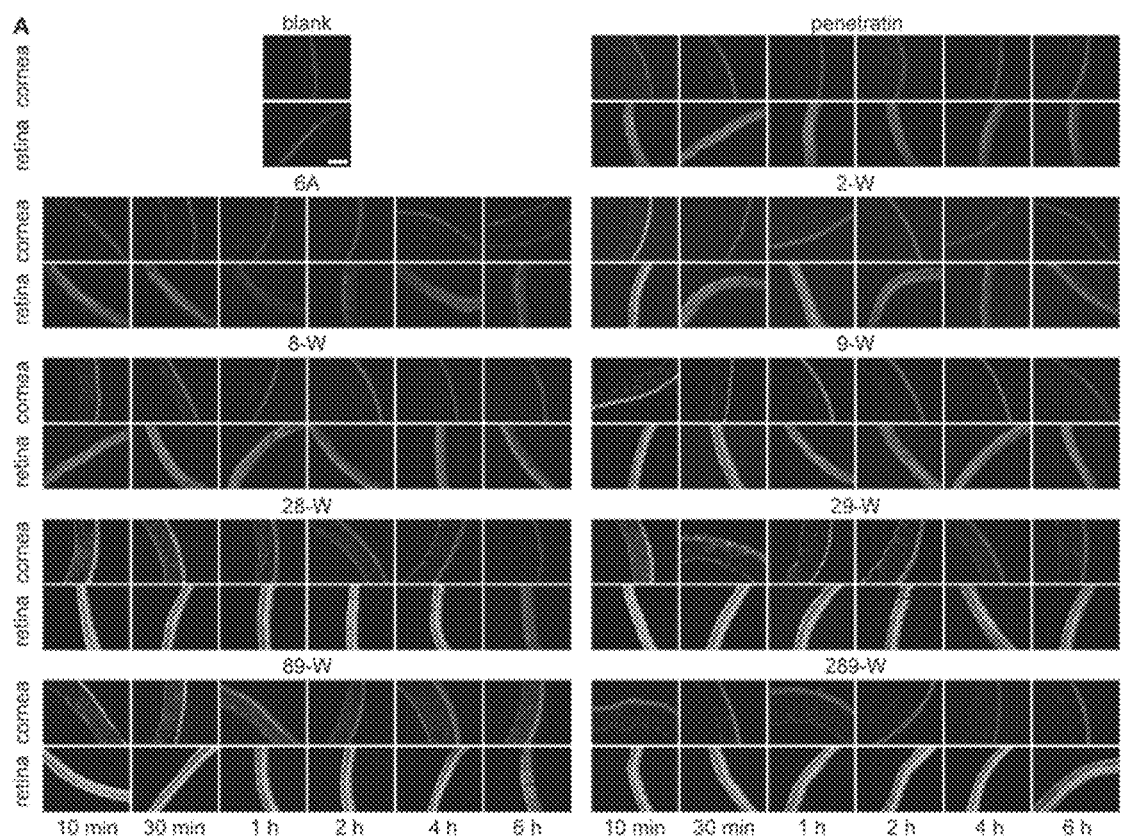
Figure 6B:
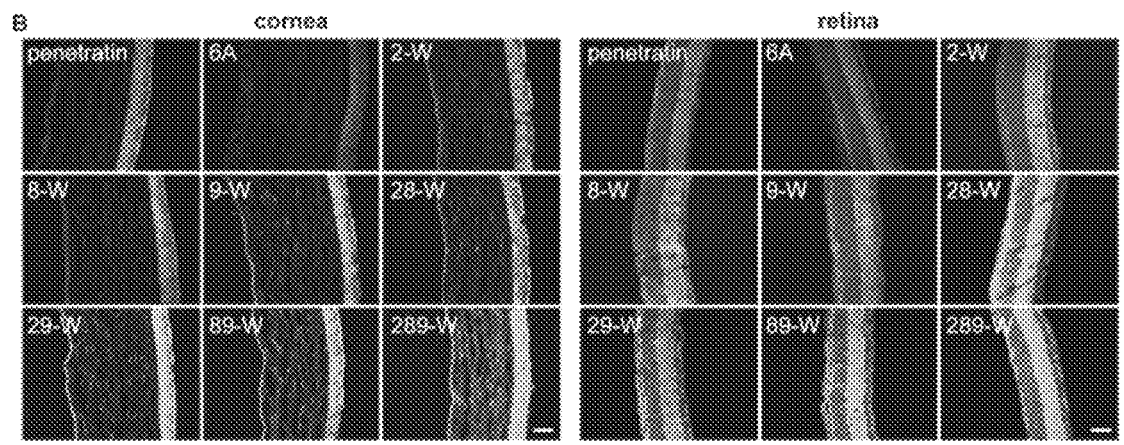

The results in FIG. 6A show that no green fluorescence signal is observed in the anterior segment (cornea) and posterior segment (retina) of the eyeball sections of the blank group of mice, indicating that the ocular tissues have no fluorescent background interference. Compared with the wild-type penetratin group, the lipophilic penetratin derivative group had stronger green FAM fluorescence signals in the anterior segment and posterior segment of the eye after 10 minutes of eye drops, indicating that lipophilic penetratin derivative has stronger eye penetrating ability, and the FAM fluorescence signal of the hydrophilic penetratin derivative group 6A weakened, indicating that its ocular permeability is weaker than that of wild-type penetratin, which is consistent with the results of in vitro experiments. Further, FIG. 6B shows that after administration via the conjunctival sac, lipophilic penetratin derivatives could be effectively distributed in the corneal stroma and inner plexiform layer of retinal of mice, while derivative 6A is significantly less distributed in the cornea than wild-type penetratin, with almost no green fluorescence signal of FAM, and the derivative 6A is also less distributed in the retina.

Figure 6C:
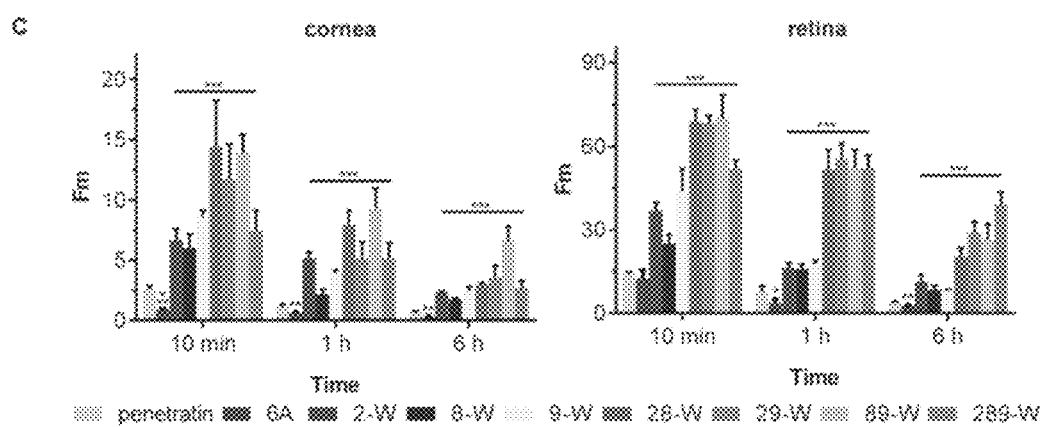

FIG. 6C semi-quantitative analysis results show that compared with wild-type penetratin, more lipophilic penetratin derivatives enter into the cornea and retina (p<0.001), and the retention time in the eye is longer. For derivatives 28-W, 29-W, 89-W and 289-W, which are more lipophilic, the retention time is up to 6 hours. For derivative 6A, the amount that entered into the eye was significantly less than that of wild-type penetratin (p<0.05), indicating that its permeability to the eye barrier was poor.

Example 8

Preparation of non-covalent complexes of Penetratin derivatives and antisense oligonucleotide drugs: taking 60 μg of antisense oligonucleotides against transforming growth factor (TGFβ2) gene (anti-TGFβ2-ASO), adding 2 mL of buffer solution, and vortexing for 30 s to fully dissolve to obtain an ASO solution with a concentration of 30 μg/mL. Taking a $5^{th}$ generation amino-terminated polyamidoamine (PAMAM, abbreviated as PG5) dendrimer in methanol 10 μL (PAMAM concentration 0.1 mg/μL), drying it with nitrogen in a 40° C. water bath, and then PAMAM was re-dissolved in 1 mL of distilled water and diluted with distilled water to obtain an experimental concentration of PAMAM solution. 1 mg of hyaluronic acid (HA) was dissolved in 1 mL of distilled water and diluted with distilled water to obtain a HA solution with a experimental concentration. Penetratin derivatives 2-M, 8-W and 9-Y (R<u>M</u>IKIWF<u>W</u>YRRMKWKK (SEQ ID NO. 68), abbreviated as Pene) were dissolved in a buffer solution to obtain a solution of a penetratin derivative with a concentration of 500 μM.

500 μL experimental concentration of PAMAM solution was added to the equal volume (500 μL) of ASO solution dropwise under vortex conditions, continue vortexing for 30 s after the dropwise addition was completed, and stabilizing the mixture at room temperature for 30 min to obtain an ASO/PG5 complex. 1 mL of the stabilized ASO/PG5 complex was added to 500 μL experimental concentration of HA solution dropwise under vortex conditions, after the dropwise addition was completed, continue vortexing for 30 s, and stabilizing the mixture at room temperature for 30 min to obtain an ASO/PG5/HA complex. 1.5 mL of the stabilized ASO/PG5/HA complex was added in 500 μL of penetratin derivative solution with a concentration of 500 μM dropwise under vortex conditions, after the dropwise addition was completed, continue vortexing for 30 s and stabilizing the mixture at room temperature for 30 min, and then ASO/PG5/HA/Pene complex was obtained.

Example 9

Ocular absorption of non-covalent complexes of penetratin derivatives and antisense oligonucleotide drugs: ASO/PG5, ASO/PG5/HA and ASO/PG5/HA/Pene complexes were prepared using fluorescently labeled ASO. All experimental groups contain 30 μg/mL of ASO. The mice were randomly divided into 3 groups, namely ASO/PG5, ASO/PG5/HA and ASO/PG5/HA/Pene groups, 12 mice in each group, and the right eye was administered dropwise with 10 μL of the experimental group solution. The drug was administered every 10 minutes, and each mouse in each group was administered a total of 3 times. After 1 h, 2 h, 6 h, and 8 h after the last administration, 3 mice were randomly selected from each group and sacrificed. The eyeballs of the mouse were removed and dehydrated in a 30% sucrose solution overnight. Sectioned perpendicular to the cornea, frozen sections were taken from the middle section of the tissue and nuclear stained with DAPI working solution. The elimination of complexes in the posterior segment of the eye was observed under a confocal microscope.

Figures 7A, 7B:
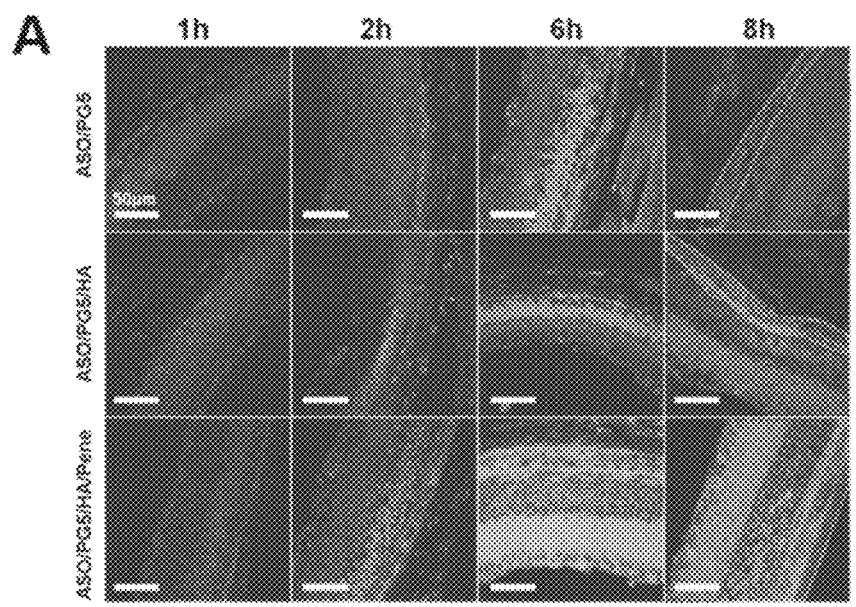

According to the observation results of frozen sections, all the ASO delivered by the three complexes were distributed in the posterior segment of the mouse eye after 1 h of eye drops, and the distribution is increased as time passed. However, only ASO delivered by ASO/PG5/HA/Pene showed obvious distribution in the posterior segment of the eye, and it was still distributed in the outer plexiform layer (OPL) and retinal pigment epithelium (RPE) after 8 hours. The results show that using the oligonucleotide complex modified with penetratin derivatives 2-M, 8-W, 9-Y can effectively deliver ASO to the posterior segment of the eye and distribute it in the retinal pigment epithelial (RPE) cell layer, and the retention time in the posterior segment of the eye is more than 8 hours (FIG. 7A). A comparison of the relative fluorescence intensities of the main ASO distribution layers is shown in FIG. 7B. A comparison of the relative fluorescence intensities of the main ASO distribution layers is shown in FIG. 7B.

Example 10

Preparation of non-covalent complex of fluorouracil modified with Penetratin derivative and antisense oligonucleotide drug dual-loading drug: taking a 5$^{th}$ generation amino-terminated polyamidoamine (PAMAM, abbreviated as PG5) dendrimer in a methanol solution of 10 μL (PAMAM concentration is 0.1 mg/μL) and drying it in a 40° C. water bath with nitrogen. PAMAM was then re-dissolved in 1 mL of distilled water and diluted with distilled water to obtain a PG5 solution with a concentration of 6.23 μM. Dissolving 1 mg of fluorouracil (Fu) in 1 mL of distilled water, after 5 min in a water bath at 40° C., vortexing to dissolve, and then diluting the mother liquor with distilled water to obtain a Fu solution with the desired concentration. Adding the Fu solution dropwise to the PG5 solution and stirring for a period of time to obtain a mixed solution. Stop stirring, transferring the mixed solution to an ultrafiltration centrifuge tube with a cut-off molecular weight of 3,000 Da, and centrifuging to remove free Fu at 3,000 rpm/min to obtain a Fu/PG5 complex solution.

30 μg of anti-TGFβ2 antisense oligonucleotide (anti-TGFβ2-ASO) was added to 3 mL of the buffer solution, and vortexing for 30 s to fully dissolve it to obtain a 10 μg/mL of ASO solution. 100 μL of ASO solution was added dropwise to the equal volume of Fu/PG5 solution under vortex conditions. After the dropwise addition was completed, the vortex was continued for 30 s and allowed to stand for 30 min at room temperature to obtain a dual/PG5 complex. After the dropwise addition was completed, the vortex was continued for 30 s, and the mixture was stabilized at room temperature for 30 min to obtain a dual/PG5 complex. Under vortex conditions, 200 μL of the stabilized dual/PG5 complex was added dropwise to 100 μL of the HA solution (containing HA g/mL). After the dropwise addition was completed, the vortex was continued for 30 s, and the mixture was allowed to stand for 30 minutes at room temperature to obtain a dual/PG5/HA complex. Under vortex conditions, 300 μL of dual/PG5/HA solution was added dropwise to 100 μL of 289-Fpenetratin derivative (R FIKIWFFFRRMKWKK (SEQ ID NO. 44), abbreviated as Pene) solution at a concentration of 300 μM. After the dropwise addition was completed, the vortex was continued for 30 s, and the mixture was allowed to stand for 30 min at room temperature to obtain a dual/PG5/HA/Pene complex.

Example 11

Evaluation of cell uptake of the non-covalent complex of fluorouracil modified with penetratin derivative and antisense oligonucleotide: Dual/PG5, dual/PG5/HA and dual/PG5/HA/Pene complexes were prepared by using fluorescently labeled PAMAM. Using free fluorescein FAM as a negative control, the uptake of non-covalent complex of dual loading drugs modified with Penetratin derivative in L929 cells was observed under a confocal microscope. Flow cytometry was used to quantitatively detect the uptake ratio of the three complexes.

Figure 8:
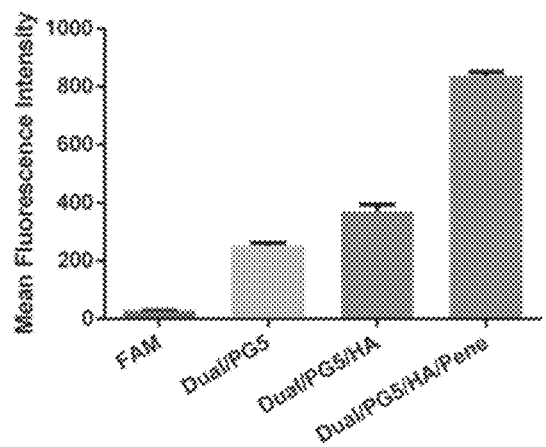
FIG. 8: Evaluation of cell uptake of non-covalent complexes of fluorouracil modified with Penetratin derivatives and antisense oligonucleotide dual loading drugs Wherein mouse fibroblasts were incubated with different prescription dual loading drugs non-covalent complexes (dual/PG5, dual/PG5/HA, dual/PG5/HA/Pene) for 4 h, and then the average fluorescence intensity of cells in each group was measured.

The average intracellular fluorescence intensity of non-covalent complex with dual loading drugs modified with the Penetratin derivative 289-F was significantly improved compared with other experimental groups. The statistical results showed that compared with dual/PG5 and dual/PG5/HA, the uptake efficiency of dual/PG5/HA/Pene in L929 cells has been increased by about 3 times and 1 times, respectively (FIG. 8).

What is claimed is:

1. A penetratin derivative comprising the amino acid sequence of:

RX$_1$IKIWFX$_2$X$_3$RRMKWKK    (SEQ ID NO: 2)

wherein X$_1$ and X$_2$ are selected from the group consisting of alanine (A), valine (V), leucine (L), isoleucine (I), proline (P), phenylalanine (F), tryptophan (W), methionine (M), α-aminobutyric acid, α-aminopentanoic acid, α-aminohexanoic acid, α-aminoheptanoic acid, and combinations thereof; and wherein X$_3$ is selected from the group consisting of asparagine (N), alanine (A), valine (V), leucine (L), isoleucine (I), proline (P), phenylalanine (F), tryptophan (W), and methionine (M).

2. A pharmaceutical composition comprising a penetratin derivative and a pharmaceutically acceptable carrier, wherein the penetratin derivative comprises the amino acid sequence of:

RX$_1$IKIWFX$_2$X$_3$RRMKWKK    (SEQ ID NO: 2)

wherein X$_1$ and X$_2$ are selected from the group consisting of alanine (A), valine (V), leucine (L), isoleucine (I), proline (P), phenylalanine (F), tryptophan (W), methionine (M), α-aminobutyric acid, α-aminopentanoic acid, α-aminohexanoic acid, α-aminoheptanoic acid, and combinations thereof; and wherein X$_3$ is selected from the group consisting of asparagine (N), alanine (A), valine (V), leucine (L), isoleucine (I), proline (P), phenylalanine (F), tryptophan (W), and methionine (M).

3. The pharmaceutical composition according to claim 2, wherein the penetratin derivative is connected through a chemical bond to form a covalent complex with a medicament having a diagnostic or therapeutic effect, or modified on a surface of a drug delivery system containing diagnostic or therapeutic drugs.

4. The pharmaceutical composition according to claim 3, wherein the medicament with a diagnostic or therapeutic effect is selected from the group consisting of: drugs for treating cataract, drugs for treating bacterial endophthalmitis, drugs for treating fungal endophthalmitis, drugs for treating glaucoma, anti-metabolites drugs, drugs for treating retinal diseases, drugs for treating optic nerve diseases, and combinations thereof.

5. The pharmaceutical composition according to claim 3, wherein the medicament with a diagnostic or therapeutic effect is selected from the group consisting of: vitamin C, vitamin E, pirenoxine, glutathione, bendazac lysine, vancomycin, ceftazidime, isepamicin, neomycin, gentamicin, erythromycin, dexamethasone, trovafloxacin, cefuroxime sodium, minocycline, voriconazole, nystatin, amphotericin B, pilocarpine, carbachol, dipivefrin, timolol, betaxolol, metipranolol, levobunolol, carteolol, dorzolamide, brinzolamide, brimonidine, latanoprost, travoprost, bimatoprost, bemeprost, tafluprost, fluorouracil, mitomycin, glucocorticoids, acyclovir, penicillin, triamcinolone acetonide, prednisolone, vitamin B1, vitamin B12, niacin, and combinations thereof.

6. The pharmaceutical composition according to claim 3, wherein the drug delivery system is selected from the group consisting of liposomes, micelles, and nanoparticles.

7. The pharmaceutical composition according to claim 3, wherein the concentration of the penetratin derivative is 1 nM-500 μM.

8. The pharmaceutical composition according to claim 3, wherein the concentration of the penetratin derivative is 10 nM-300 μM.

9. The pharmaceutical composition according to claim 3, wherein the concentration of the penetratin derivative is 100 nM-100 μM.

10. The pharmaceutical composition according to claim 2, wherein a non-covalent complex is formed by self-assembly with a biological macromolecular drug.

11. The pharmaceutical composition according to claim 10, wherein the biological macromolecular drug is selected from the group consisting of: monoclonal antibody drugs, polypeptide protein drugs, and combinations thereof.

12. The pharmaceutical composition according to claim 11, wherein the anti-vascular endothelial growth factor (anti-VEGF) fusion protein is Conbercept.

13. The pharmaceutical composition according to claim 10, wherein the biological macromolecular drug is selected from the group consisting of: plasmid DNA (pDNA), pegaptanib, bevasiranib, antisense oligonucleotide, and combinations thereof.

14. The pharmaceutical composition according to claim 10, wherein the biological macromolecular drug is selected from the group consisting of: Bevacizumab, Ramucirumab, anti-vascular endothelial growth factor (anti-VEGF) fusion protein, epidermal growth factor (EGF), defensin, interferon, cyclosporine, and combinations thereof.

15. A method of intraocular delivery to a subject comprising intraocularly administering to said subject the pharmaceutical composition of claim 3.

16. The method according to claim 15, wherein the concentration of the penetratin derivative is 1 nM-500 µM.

17. The method according to claim 15, wherein the concentration of the penetratin derivative is 10 nM-300 µM.

18. The method according to claim 15, wherein the concentration of the penetratin derivative is 100 nM-100 µM.

* * * * *

SEQUENCE LISTING

<160> NUMBER OF SEQ ID NOS: 87

<210> SEQ ID NO 1
<211> LENGTH: 16
<212> TYPE: PRT
<213> ORGANISM: Drosophila melanogaster

<400> SEQUENCE: 1

Arg Gln Ile Lys Ile Trp Phe Gln Asn Arg Arg Met Lys Trp Lys Lys
1               5                   10                  15

<210> SEQ ID NO 2
<211> LENGTH: 16
<212> TYPE: PRT
<213> ORGANISM: Artificial sequence
<220> FEATURE:
<223> OTHER INFORMATION: penetratin derivative
<220> FEATURE:
<221> NAME/KEY: misc_feature
<222> LOCATION: (2)..(2)
<223> OTHER INFORMATION: Xaa is A,V,L,I,P,F,W,M,aminobutyric acid,

```
       aminopentanoic acid,aminohexanoic acid,or aminoheptanoic acid
<220> FEATURE:
<221> NAME/KEY: misc_feature
<222> LOCATION: (8)..(9)
<223> OTHER INFORMATION: Xaa is A,V,L,I,P,F,W,M,aminobutyric acid,
       aminopentanoic acid,aminohexanoic acid,or aminoheptanoic acid

<400> SEQUENCE: 2

Arg Xaa Ile Lys Ile Trp Phe Xaa Xaa Arg Arg Met Lys Trp Lys Lys
1               5                   10                  15

<210> SEQ ID NO 3
<211> LENGTH: 16
<212> TYPE: PRT
<213> ORGANISM: Artificial sequence
<220> FEATURE:
<223> OTHER INFORMATION: penetratin derivative

<400> SEQUENCE: 3

Arg Ala Ile Lys Ile Trp Phe Gln Asn Arg Arg Met Lys Trp Lys Lys
1               5                   10                  15

<210> SEQ ID NO 4
<211> LENGTH: 16
<212> TYPE: PRT
<213> ORGANISM: Artificial sequence
<220> FEATURE:
<223> OTHER INFORMATION: penetratin derivative

<400> SEQUENCE: 4

Arg Val Ile Lys Ile Trp Phe Gln Asn Arg Arg Met Lys Trp Lys Lys
1               5                   10                  15

<210> SEQ ID NO 5
<211> LENGTH: 16
<212> TYPE: PRT
<213> ORGANISM: Artificial sequence
<220> FEATURE:
<223> OTHER INFORMATION: penetratin derivative

<400> SEQUENCE: 5

Arg Gln Ile Lys Ile Trp Phe Ala Asn Arg Arg Met Lys Trp Lys Lys
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: penetratin derivative

<400> SEQUENCE: 6

Arg Gln Ile Lys Ile Trp Phe Val Asn Arg Arg Met Lys Trp Lys Lys
1               5                   10                  15

<210> SEQ ID NO 7
<211> LENGTH: 16
<212> TYPE: PRT
<213> ORGANISM: Artificial sequence
<220> FEATURE:
<223> OTHER INFORMATION: penetratin derivative

<400> SEQUENCE: 7

Arg Gln Ile Lys Ile Trp Phe Gln Ala Arg Arg Met Lys Trp Lys Lys
1               5                   10                  15

<210> SEQ ID NO 8
```

```
<211> LENGTH: 16
<212> TYPE: PRT
<213> ORGANISM: Artificial sequence
<220> FEATURE:
<223> OTHER INFORMATION: penetratin derivative

<400> SEQUENCE: 8

Arg Gln Ile Lys Ile Trp Phe Gln Val Arg Arg Met Lys Trp Lys Lys
1               5                   10                  15

<210> SEQ ID NO 9
<211> LENGTH: 16
<212> TYPE: PRT
<213> ORGANISM: Artificial sequence
<220> FEATURE:
<223> OTHER INFORMATION: penetratin derivative

<400> SEQUENCE: 9

Arg Ala Ile Lys Ile Trp Phe Ala Asn Arg Arg Met Lys Trp Lys Lys
1               5                   10                  15

<210> SEQ ID NO 10
<211> LENGTH: 16
<212> TYPE: PRT
<213> ORGANISM: Artificial sequence
<220> FEATURE:
<223> OTHER INFORMATION: penetratin derivative

<400> SEQUENCE: 10

Arg Val Ile Lys Ile Trp Phe Val Asn Arg Arg Met Lys Trp Lys Lys
1               5                   10                  15

<210> SEQ ID NO 11
<211> LENGTH: 16
<212> TYPE: PRT
<213> ORGANISM: Artificial sequence
<220> FEATURE:
<223> OTHER INFORMATION: penetratin derivative

<400> SEQUENCE: 11

Arg Ala Ile Lys Ile Trp Phe Gln Ala Arg Arg Met Lys Trp Lys Lys
1               5                   10                  15

<210> SEQ ID NO 12
<211> LENGTH: 16
<212> TYPE: PRT
<213> ORGANISM: Artificial sequence
<220> FEATURE:
<223> OTHER INFORMATION: penetratin derivative

<400> SEQUENCE: 12

Arg Val Ile Lys Ile Trp Phe Gln Val Arg Arg Met Lys Trp Lys Lys
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: penetratin derivative

<400> SEQUENCE: 13

Arg Gln Ile Lys Ile Trp Phe Ala Ala Arg Arg Met Lys Trp Lys Lys
1               5                   10                  15

<210> SEQ ID NO 14
<211> LENGTH: 16
```

```
<212> TYPE: PRT
<213> ORGANISM: Artificial sequence
<220> FEATURE:
<223> OTHER INFORMATION: penetratin derivative

<400> SEQUENCE: 14

Arg Gln Ile Lys Ile Trp Phe Val Val Arg Arg Met Lys Trp Lys Lys
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: penetratin derivative

<400> SEQUENCE: 15

Arg Ala Ile Lys Ile Trp Phe Ala Ala Arg Arg Met Lys Trp Lys Lys
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: penetratin derivative

<400> SEQUENCE: 16

Arg Val Ile Lys Ile Trp Phe Val Val Arg Arg Met Lys Trp Lys Lys
1               5                   10                  15

<210> SEQ ID NO 17
<211> LENGTH: 16
<212> TYPE: PRT
<213> ORGANISM: Artificial sequence
<220> FEATURE:
<223> OTHER INFORMATION: penetratin derivative

<400> SEQUENCE: 17

Arg Leu Ile Lys Ile Trp Phe Gln Asn Arg Arg Met Lys Trp Lys Lys
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: penetratin derivative

<400> SEQUENCE: 18

Arg Ile Ile Lys Ile Trp Phe Gln Asn Arg Arg Met Lys Trp Lys Lys
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: penetratin derivative

<400> SEQUENCE: 19

Arg Gln Ile Lys Ile Trp Phe Leu Asn Arg Arg Met Lys Trp Lys Lys
1               5                   10                  15

<210> SEQ ID NO 20
<211> LENGTH: 16
<212> TYPE: PRT
```

```
<213> ORGANISM: Artificial sequence
<220> FEATURE:
<223> OTHER INFORMATION: penetratin derivative

<400> SEQUENCE: 20

Arg Gln Ile Lys Ile Trp Phe Ile Asn Arg Arg Met Lys Trp Lys Lys
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: penetratin derivative

<400> SEQUENCE: 21

Arg Gln Ile Lys Ile Trp Phe Gln Leu Arg Arg Met Lys Trp Lys Lys
1               5                   10                  15

<210> SEQ ID NO 22
<211> LENGTH: 16
<212> TYPE: PRT
<213> ORGANISM: Artificial sequence
<220> FEATURE:
<223> OTHER INFORMATION: penetratin derivative

<400> SEQUENCE: 22

Arg Gln Ile Lys Ile Trp Phe Gln Ile Arg Arg Met Lys Trp Lys Lys
1               5                   10                  15

<210> SEQ ID NO 23
<211> LENGTH: 16
<212> TYPE: PRT
<213> ORGANISM: Artificial sequence
<220> FEATURE:
<223> OTHER INFORMATION: penetratin derivative

<400> SEQUENCE: 23

Arg Leu Ile Lys Ile Trp Phe Leu Asn Arg Arg Met Lys Trp Lys Lys
1               5                   10                  15

<210> SEQ ID NO 24
<211> LENGTH: 16
<212> TYPE: PRT
<213> ORGANISM: Artificial sequence
<220> FEATURE:
<223> OTHER INFORMATION: penetratin derivative

<400> SEQUENCE: 24

Arg Ile Ile Lys Ile Trp Phe Ile Asn Arg Arg Met Lys Trp Lys Lys
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: penetratin derivative

<400> SEQUENCE: 25

Arg Leu Ile Lys Ile Trp Phe Gln Leu Arg Arg Met Lys Trp Lys Lys
1               5                   10                  15

<210> SEQ ID NO 26
<211> LENGTH: 16
<212> TYPE: PRT
<213> ORGANISM: Artificial sequence
```

<220> FEATURE:
<223> OTHER INFORMATION: penetratin derivative

<400> SEQUENCE: 26

Arg Ile Ile Lys Ile Trp Phe Gln Ile Arg Arg Met Lys Trp Lys Lys
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: penetratin derivative

<400> SEQUENCE: 27

Arg Gln Ile Lys Ile Trp Phe Leu Leu Arg Arg Met Lys Trp Lys Lys
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: penetratin derivative

<400> SEQUENCE: 28

Arg Gln Ile Lys Ile Trp Phe Ile Ile Arg Arg Met Lys Trp Lys Lys
1               5                   10                  15

<210> SEQ ID NO 29
<211> LENGTH: 16
<212> TYPE: PRT
<213> ORGANISM: Artificial sequence
<220> FEATURE:
<223> OTHER INFORMATION: penetratin derivative

<400> SEQUENCE: 29

Arg Leu Ile Lys Ile Trp Phe Leu Leu Arg Arg Met Lys Trp Lys Lys
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: penetratin derivative

<400> SEQUENCE: 30

Arg Ile Ile Lys Ile Trp Phe Ile Ile Arg Arg Met Lys Trp Lys Lys
1               5                   10                  15

<210> SEQ ID NO 31
<211> LENGTH: 16
<212> TYPE: PRT
<213> ORGANISM: Artificial sequence
<220> FEATURE:
<223> OTHER INFORMATION: penetratin derivative

<400> SEQUENCE: 31

Arg Pro Ile Lys Ile Trp Phe Gln Asn Arg Arg Met Lys Trp Lys Lys
1               5                   10                  15

<210> SEQ ID NO 32
<211> LENGTH: 16
<212> TYPE: PRT
<213> ORGANISM: Artificial sequence
<220> FEATURE:

<223> OTHER INFORMATION: penetratin derivative

<400> SEQUENCE: 32

Arg Phe Ile Lys Ile Trp Phe Gln Asn Arg Arg Met Lys Trp Lys Lys
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: penetratin derivative

<400> SEQUENCE: 33

Arg Gln Ile Lys Ile Trp Phe Pro Asn Arg Arg Met Lys Trp Lys Lys
1               5                   10                  15

<210> SEQ ID NO 34
<211> LENGTH: 16
<212> TYPE: PRT
<213> ORGANISM: Artificial sequence
<220> FEATURE:
<223> OTHER INFORMATION: penetratin derivative

<400> SEQUENCE: 34

Arg Gln Ile Lys Ile Trp Phe Phe Asn Arg Arg Met Lys Trp Lys Lys
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: penetratin derivative

<400> SEQUENCE: 35

Arg Gln Ile Lys Ile Trp Phe Gln Pro Arg Arg Met Lys Trp Lys Lys
1               5                   10                  15

<210> SEQ ID NO 36
<211> LENGTH: 16
<212> TYPE: PRT
<213> ORGANISM: Artificial sequence
<220> FEATURE:
<223> OTHER INFORMATION: penetratin derivative

<400> SEQUENCE: 36

Arg Gln Ile Lys Ile Trp Phe Gln Phe Arg Arg Met Lys Trp Lys Lys
1               5                   10                  15

<210> SEQ ID NO 37
<211> LENGTH: 16
<212> TYPE: PRT
<213> ORGANISM: Artificial sequence
<220> FEATURE:
<223> OTHER INFORMATION: penetratin derivative

<400> SEQUENCE: 37

Arg Pro Ile Lys Ile Trp Phe Pro Asn Arg Arg Met Lys Trp Lys Lys
1               5                   10                  15

<210> SEQ ID NO 38
<211> LENGTH: 16
<212> TYPE: PRT
<213> ORGANISM: Artificial sequence
<220> FEATURE:
<223> OTHER INFORMATION: penetratin derivative

<400> SEQUENCE: 38

Arg Phe Ile Lys Ile Trp Phe Asn Arg Arg Met Lys Trp Lys Lys
1               5                   10                  15

<210> SEQ ID NO 39
<211> LENGTH: 16
<212> TYPE: PRT
<213> ORGANISM: Artificial sequence
<220> FEATURE:
<223> OTHER INFORMATION: penetratin derivative

<400> SEQUENCE: 39

Arg Pro Ile Lys Ile Trp Phe Gln Pro Arg Arg Met Lys Trp Lys Lys
1               5                   10                  15

<210> SEQ ID NO 40
<211> LENGTH: 16
<212> TYPE: PRT
<213> ORGANISM: Artificial sequence
<220> FEATURE:
<223> OTHER INFORMATION: penetratin derivative

<400> SEQUENCE: 40

Arg Phe Ile Lys Ile Trp Phe Gln Phe Arg Arg Met Lys Trp Lys Lys
1               5                   10                  15

<210> SEQ ID NO 41
<211> LENGTH: 16
<212> TYPE: PRT
<213> ORGANISM: Artificial sequence
<220> FEATURE:
<223> OTHER INFORMATION: penetratin derivative

<400> SEQUENCE: 41

Arg Gln Ile Lys Ile Trp Phe Pro Pro Arg Arg Met Lys Trp Lys Lys
1               5                   10                  15

<210> SEQ ID NO 42
<211> LENGTH: 16
<212> TYPE: PRT
<213> ORGANISM: Artificial sequence
<220> FEATURE:
<223> OTHER INFORMATION: penetratin derivative

<400> SEQUENCE: 42

Arg Gln Ile Lys Ile Trp Phe Phe Phe Arg Arg Met Lys Trp Lys Lys
1               5                   10                  15

<210> SEQ ID NO 43
<211> LENGTH: 16
<212> TYPE: PRT
<213> ORGANISM: Artificial sequence
<220> FEATURE:
<223> OTHER INFORMATION: penetratin derivative

<400> SEQUENCE: 43

Arg Pro Ile Lys Ile Trp Phe Pro Pro Arg Arg Met Lys Trp Lys Lys
1               5                   10                  15

<210> SEQ ID NO 44
<211> LENGTH: 16
<212> TYPE: PRT
<213> ORGANISM: Artificial sequence
<220> FEATURE:
<223> OTHER INFORMATION: penetratin derivative

```
<400> SEQUENCE: 44

Arg Phe Ile Lys Ile Trp Phe Phe Arg Arg Met Lys Trp Lys Lys
1               5                   10                  15

<210> SEQ ID NO 45
<211> LENGTH: 16
<212> TYPE: PRT
<213> ORGANISM: Artificial sequence
<220> FEATURE:
<223> OTHER INFORMATION: penetratin derivative

<400> SEQUENCE: 45

Arg Trp Ile Lys Ile Trp Phe Gln Asn Arg Arg Met Lys Trp Lys Lys
1               5                   10                  15

<210> SEQ ID NO 46
<211> LENGTH: 16
<212> TYPE: PRT
<213> ORGANISM: Artificial sequence
<220> FEATURE:
<223> OTHER INFORMATION: penetratin derivative

<400> SEQUENCE: 46

Arg Met Ile Lys Ile Trp Phe Gln Asn Arg Arg Met Lys Trp Lys Lys
1               5                   10                  15

<210> SEQ ID NO 47
<211> LENGTH: 16
<212> TYPE: PRT
<213> ORGANISM: Artificial sequence
<220> FEATURE:
<223> OTHER INFORMATION: penetratin derivative

<400> SEQUENCE: 47

Arg Gln Ile Lys Ile Trp Phe Trp Asn Arg Arg Met Lys Trp Lys Lys
1               5                   10                  15

<210> SEQ ID NO 48
<211> LENGTH: 16
<212> TYPE: PRT
<213> ORGANISM: Artificial sequence
<220> FEATURE:
<223> OTHER INFORMATION: penetratin derivative

<400> SEQUENCE: 48

Arg Gln Ile Lys Ile Trp Phe Met Asn Arg Arg Met Lys Trp Lys Lys
1               5                   10                  15

<210> SEQ ID NO 49
<211> LENGTH: 16
<212> TYPE: PRT
<213> ORGANISM: Artificial sequence
<220> FEATURE:
<223> OTHER INFORMATION: penetratin derivative

<400> SEQUENCE: 49

Arg Gln Ile Lys Ile Trp Phe Gln Trp Arg Arg Met Lys Trp Lys Lys
1               5                   10                  15

<210> SEQ ID NO 50
<211> LENGTH: 16
<212> TYPE: PRT
<213> ORGANISM: Artificial sequence
<220> FEATURE:
<223> OTHER INFORMATION: penetratin derivative

<400> SEQUENCE: 50
```

Arg Gln Ile Lys Ile Trp Phe Gln Met Arg Arg Met Lys Trp Lys Lys
1               5                   10                  15

<210> SEQ ID NO 51
<211> LENGTH: 16
<212> TYPE: PRT
<213> ORGANISM: Artificial sequence
<220> FEATURE:
<223> OTHER INFORMATION: penetratin derivative

<400> SEQUENCE: 51

Arg Trp Ile Lys Ile Trp Phe Trp Asn Arg Arg Met Lys Trp Lys Lys
1               5                   10                  15

<210> SEQ ID NO 52
<211> LENGTH: 16
<212> TYPE: PRT
<213> ORGANISM: Artificial sequence
<220> FEATURE:
<223> OTHER INFORMATION: penetratin derivative

<400> SEQUENCE: 52

Arg Met Ile Lys Ile Trp Phe Met Asn Arg Arg Met Lys Trp Lys Lys
1               5                   10                  15

<210> SEQ ID NO 53
<211> LENGTH: 16
<212> TYPE: PRT
<213> ORGANISM: Artificial sequence
<220> FEATURE:
<223> OTHER INFORMATION: penetratin derivative

<400> SEQUENCE: 53

Arg Trp Ile Lys Ile Trp Phe Gln Trp Arg Arg Met Lys Trp Lys Lys
1               5                   10                  15

<210> SEQ ID NO 54
<211> LENGTH: 16
<212> TYPE: PRT
<213> ORGANISM: Artificial sequence
<220> FEATURE:
<223> OTHER INFORMATION: penetratin derivative

<400> SEQUENCE: 54

Arg Met Ile Lys Ile Trp Phe Gln Met Arg Arg Met Lys Trp Lys Lys
1               5                   10                  15

<210> SEQ ID NO 55
<211> LENGTH: 16
<212> TYPE: PRT
<213> ORGANISM: Artificial sequence
<220> FEATURE:
<223> OTHER INFORMATION: penetratin derivative

<400> SEQUENCE: 55

Arg Gln Ile Lys Ile Trp Phe Trp Trp Arg Arg Met Lys Trp Lys Lys
1               5                   10                  15

<210> SEQ ID NO 56
<211> LENGTH: 16
<212> TYPE: PRT
<213> ORGANISM: Artificial sequence
<220> FEATURE:
<223> OTHER INFORMATION: penetratin derivative

<400> SEQUENCE: 56

```
Arg Gln Ile Lys Ile Trp Phe Met Met Arg Arg Met Lys Trp Lys Lys
1               5                   10                  15
```

<210> SEQ ID NO 57
<211> LENGTH: 16
<212> TYPE: PRT
<213> ORGANISM: Artificial sequence
<220> FEATURE:
<223> OTHER INFORMATION: penetratin derivative

<400> SEQUENCE: 57

```
Arg Trp Ile Lys Ile Trp Phe Trp Trp Arg Arg Met Lys Trp Lys Lys
1               5                   10                  15
```

<210> SEQ ID NO 58
<211> LENGTH: 16
<212> TYPE: PRT
<213> ORGANISM: Artificial sequence
<220> FEATURE:
<223> OTHER INFORMATION: penetratin derivative

<400> SEQUENCE: 58

```
Arg Met Ile Lys Ile Trp Phe Met Met Arg Arg Met Lys Trp Lys Lys
1               5                   10                  15
```

<210> SEQ ID NO 59
<211> LENGTH: 16
<212> TYPE: PRT
<213> ORGANISM: Artificial sequence
<220> FEATURE:
<223> OTHER INFORMATION: penetratin derivative

<400> SEQUENCE: 59

```
Arg Ala Ile Lys Ile Trp Phe Val Asn Arg Arg Met Lys Trp Lys Lys
1               5                   10                  15
```

<210> SEQ ID NO 60
<211> LENGTH: 16
<212> TYPE: PRT
<213> ORGANISM: Artificial sequence
<220> FEATURE:
<223> OTHER INFORMATION: penetratin derivative

<400> SEQUENCE: 60

```
Arg Phe Ile Lys Ile Trp Phe Gln Trp Arg Arg Met Lys Trp Lys Lys
1               5                   10                  15
```

<210> SEQ ID NO 61
<211> LENGTH: 16
<212> TYPE: PRT
<213> ORGANISM: Artificial sequence
<220> FEATURE:
<223> OTHER INFORMATION: penetratin derivative

<400> SEQUENCE: 61

```
Arg Val Ile Lys Ile Trp Phe Ala Asn Arg Arg Met Lys Trp Lys Lys
1               5                   10                  15
```

<210> SEQ ID NO 62
<211> LENGTH: 16
<212> TYPE: PRT
<213> ORGANISM: Artificial sequence
<220> FEATURE:
<223> OTHER INFORMATION: penetratin derivative

<400> SEQUENCE: 62

```
Arg Trp Ile Lys Ile Trp Phe Gln Phe Arg Arg Met Lys Trp Lys Lys
```

```
<210> SEQ ID NO 63
<211> LENGTH: 16
<212> TYPE: PRT
<213> ORGANISM: Artificial sequence
<220> FEATURE:
<223> OTHER INFORMATION: penetratin derivative

<400> SEQUENCE: 63

Arg Val Ile Lys Ile Trp Phe Gln Leu Arg Arg Met Lys Trp Lys Lys
1               5                   10                  15

<210> SEQ ID NO 64
<211> LENGTH: 16
<212> TYPE: PRT
<213> ORGANISM: Artificial sequence
<220> FEATURE:
<223> OTHER INFORMATION: penetratin derivative

<400> SEQUENCE: 64

Arg Trp Ile Lys Ile Trp Phe Gln Met Arg Arg Met Lys Trp Lys Lys
1               5                   10                  15

<210> SEQ ID NO 65
<211> LENGTH: 16
<212> TYPE: PRT
<213> ORGANISM: Artificial sequence
<220> FEATURE:
<223> OTHER INFORMATION: penetratin derivative

<400> SEQUENCE: 65

Arg Leu Ile Lys Ile Trp Phe Gln Val Arg Arg Met Lys Trp Lys Lys
1               5                   10                  15

<210> SEQ ID NO 66
<211> LENGTH: 16
<212> TYPE: PRT
<213> ORGANISM: Artificial sequence
<220> FEATURE:
<223> OTHER INFORMATION: penetratin derivative

<400> SEQUENCE: 66

Arg Met Ile Lys Ile Trp Phe Gln Trp Arg Arg Met Lys Trp Lys Lys
1               5                   10                  15

<210> SEQ ID NO 67
<211> LENGTH: 16
<212> TYPE: PRT
<213> ORGANISM: Artificial sequence
<220> FEATURE:
<223> OTHER INFORMATION: penetratin derivative

<400> SEQUENCE: 67

Arg Leu Ile Lys Ile Trp Phe Gln Ile Arg Arg Met Lys Trp Lys Lys
1               5                   10                  15

<210> SEQ ID NO 68
<211> LENGTH: 16
<212> TYPE: PRT
<213> ORGANISM: Artificial sequence
<220> FEATURE:
<223> OTHER INFORMATION: penetratin derivative

<400> SEQUENCE: 68

Arg Met Ile Lys Ile Trp Phe Trp Tyr Arg Arg Met Lys Trp Lys Lys
1               5                   10                  15
```

<210> SEQ ID NO 69
<211> LENGTH: 16
<212> TYPE: PRT
<213> ORGANISM: Artificial sequence
<220> FEATURE:
<223> OTHER INFORMATION: penetratin derivative

<400> SEQUENCE: 69

Arg Ile Ile Lys Ile Trp Phe Gln Leu Arg Arg Met Lys Trp Lys Lys
1               5                   10                  15

<210> SEQ ID NO 70
<211> LENGTH: 16
<212> TYPE: PRT
<213> ORGANISM: Artificial sequence
<220> FEATURE:
<223> OTHER INFORMATION: penetratin derivative

<400> SEQUENCE: 70

Arg Trp Ile Lys Ile Trp Phe Tyr Pro Arg Arg Met Lys Trp Lys Lys
1               5                   10                  15

<210> SEQ ID NO 71
<211> LENGTH: 16
<212> TYPE: PRT
<213> ORGANISM: Artificial sequence
<220> FEATURE:
<223> OTHER INFORMATION: penetratin derivative

<400> SEQUENCE: 71

Arg Ile Ile Lys Ile Trp Phe Pro Asn Arg Arg Met Lys Trp Lys Lys
1               5                   10                  15

<210> SEQ ID NO 72
<211> LENGTH: 16
<212> TYPE: PRT
<213> ORGANISM: Artificial sequence
<220> FEATURE:
<223> OTHER INFORMATION: penetratin derivative

<400> SEQUENCE: 72

Arg Tyr Ile Lys Ile Trp Phe Pro Ile Arg Arg Met Lys Trp Lys Lys
1               5                   10                  15

<210> SEQ ID NO 73
<211> LENGTH: 16
<212> TYPE: PRT
<213> ORGANISM: Artificial sequence
<220> FEATURE:
<223> OTHER INFORMATION: penetratin derivative

<400> SEQUENCE: 73

Arg Pro Ile Lys Ile Trp Phe Ile Asn Arg Arg Met Lys Trp Lys Lys
1               5                   10                  15

<210> SEQ ID NO 74
<211> LENGTH: 16
<212> TYPE: PRT
<213> ORGANISM: Artificial sequence
<220> FEATURE:
<223> OTHER INFORMATION: penetratin derivative

<400> SEQUENCE: 74

Arg Pro Ile Lys Ile Trp Phe Ile Leu Arg Arg Met Lys Trp Lys Lys
1               5                   10                  15

<210> SEQ ID NO 75
<211> LENGTH: 16
<212> TYPE: PRT
<213> ORGANISM: Artificial sequence
<220> FEATURE:
<223> OTHER INFORMATION: penetratin derivative

<400> SEQUENCE: 75

Arg Pro Ile Lys Ile Trp Phe Phe Asn Arg Arg Met Lys Trp Lys Lys
1               5                   10                  15

<210> SEQ ID NO 76
<211> LENGTH: 16
<212> TYPE: PRT
<213> ORGANISM: Artificial sequence
<220> FEATURE:
<223> OTHER INFORMATION: penetratin derivative

<400> SEQUENCE: 76

Arg Ile Ile Lys Ile Trp Phe Leu Val Arg Arg Met Lys Trp Lys Lys
1               5                   10                  15

<210> SEQ ID NO 77
<211> LENGTH: 16
<212> TYPE: PRT
<213> ORGANISM: Artificial sequence
<220> FEATURE:
<223> OTHER INFORMATION: penetratin derivative

<400> SEQUENCE: 77

Arg Phe Ile Lys Ile Trp Phe Pro Asn Arg Arg Met Lys Trp Lys Lys
1               5                   10                  15

<210> SEQ ID NO 78
<211> LENGTH: 16
<212> TYPE: PRT
<213> ORGANISM: Artificial sequence
<220> FEATURE:
<223> OTHER INFORMATION: penetratin derivative

<400> SEQUENCE: 78

Arg Leu Ile Lys Ile Trp Phe Val Ala Arg Arg Met Lys Trp Lys Lys
1               5                   10                  15

<210> SEQ ID NO 79
<211> LENGTH: 17
<212> TYPE: PRT
<213> ORGANISM: Artificial sequence
<220> FEATURE:
<223> OTHER INFORMATION: penetratin derivative

<400> SEQUENCE: 79

Arg Gln Ile Lys Ile Trp Phe Gln Asn Arg Arg Met Lys Trp Lys Lys
1               5                   10                  15

Lys

<210> SEQ ID NO 80
<211> LENGTH: 17
<212> TYPE: PRT
<213> ORGANISM: Artificial sequence
<220> FEATURE:
<223> OTHER INFORMATION: penetratin derivative

<400> SEQUENCE: 80

Arg Trp Ile Lys Ile Trp Phe Gln Asn Arg Arg Met Lys Trp Lys Lys
1               5                   10                  15

Lys

<210> SEQ ID NO 81
<211> LENGTH: 17
<212> TYPE: PRT
<213> ORGANISM: Artificial sequence
<220> FEATURE:
<223> OTHER INFORMATION: penetratin derivative

<400> SEQUENCE: 81

Arg Gln Ile Lys Ile Trp Phe Trp Asn Arg Arg Met Lys Trp Lys Lys
1               5                   10                  15

Lys

<210> SEQ ID NO 82
<211> LENGTH: 17
<212> TYPE: PRT
<213> ORGANISM: Artificial sequence
<220> FEATURE:
<223> OTHER INFORMATION: penetratin derivative

<400> SEQUENCE: 82

Arg Gln Ile Lys Ile Trp Phe Gln Trp Arg Arg Met Lys Trp Lys Lys
1               5                   10                  15

Lys

<210> SEQ ID NO 83
<211> LENGTH: 17
<212> TYPE: PRT
<213> ORGANISM: Artificial sequence
<220> FEATURE:
<223> OTHER INFORMATION: penetratin derivative

<400> SEQUENCE: 83

Arg Trp Ile Lys Ile Trp Phe Trp Asn Arg Arg Met Lys Trp Lys Lys
1               5                   10                  15

Lys

<210> SEQ ID NO 84
<211> LENGTH: 17
<212> TYPE: PRT
<213> ORGANISM: Artificial sequence
<220> FEATURE:
<223> OTHER INFORMATION: penetratin derivative

<400> SEQUENCE: 84

Arg Trp Ile Lys Ile Trp Phe Gln Trp Arg Arg Met Lys Trp Lys Lys
1               5                   10                  15

Lys

<210> SEQ ID NO 85
<211> LENGTH: 17
<212> TYPE: PRT
<213> ORGANISM: Artificial sequence
<220> FEATURE:
<223> OTHER INFORMATION: penetratin derivative

<400> SEQUENCE: 85

Arg Gln Ile Lys Ile Trp Phe Trp Trp Arg Arg Met Lys Trp Lys Lys
1               5                   10                  15

Lys

```
<210> SEQ ID NO 86
<211> LENGTH: 17
<212> TYPE: PRT
<213> ORGANISM: Artificial sequence
<220> FEATURE:
<223> OTHER INFORMATION: penetratin derivative

<400> SEQUENCE: 86

Arg Trp Ile Lys Ile Trp Phe Trp Trp Arg Arg Met Lys Trp Lys Lys
1               5                   10                  15

Lys

<210> SEQ ID NO 87
<211> LENGTH: 17
<212> TYPE: PRT
<213> ORGANISM: Artificial sequence
<220> FEATURE:
<223> OTHER INFORMATION: penetratin derivative

<400> SEQUENCE: 87

Arg Gln Ala Lys Ala Ala Ala Gln Asn Arg Arg Ala Lys Ala Lys Lys
1               5                   10                  15

Lys
```